US011123427B2

(12) United States Patent
Garry et al.

(10) Patent No.: US 11,123,427 B2
(45) Date of Patent: *Sep. 21, 2021

(54) IMMUNOPROTECTIVE PRIMARY MESENCHYMAL STEM CELLS AND METHODS

(71) Applicants: THE ADMINISTRATORS OF THE TULANE EDUCATIONAL FUND, New Orleans, LA (US); AUTOIMMUNE TECHNOLOGIES, INC., New Orleans, LA (US)

(72) Inventors: Robert Francis Garry, New Orleans, LA (US); Luis Manuel Branco, Germantown, MD (US); Bruce Alan Bunnell, Mandeville, LA (US); Russell B. Wilson, Mandeville, LA (US); Samuel E. Hopkins, Raleigh, NC (US)

(73) Assignees: THE ADMINISTRATORS OF THE TULANE EDUCATIONAL FUND, New Orleans, LA (US); AUTOIMMUNE TECHNOLOGIES, LLC, New Orleans, LA (US)

( * ) Notice: Subject to any disclaimer, the term of this patent is extended or adjusted under 35 U.S.C. 154(b) by 284 days.

This patent is subject to a terminal disclaimer.

(21) Appl. No.: 16/426,911

(22) Filed: May 30, 2019

(65) Prior Publication Data
US 2019/0282694 A1 Sep. 19, 2019

Related U.S. Application Data

(63) Continuation of application No. 14/802,247, filed on Jul. 17, 2015, now Pat. No. 10,357,562, which is a continuation of application No. 13/826,285, filed on Mar. 14, 2013, now Pat. No. 9,101,597.

(51) Int. Cl.
*A61K 39/42* (2006.01)
*A61K 35/28* (2015.01)
*C12N 5/0775* (2010.01)
*C07K 16/10* (2006.01)
*G01N 33/68* (2006.01)

(52) U.S. Cl.
CPC .............. *A61K 39/42* (2013.01); *A61K 35/28* (2013.01); *C07K 16/10* (2013.01); *C12N 5/0667* (2013.01); *G01N 33/6854* (2013.01); *C07K 2317/76* (2013.01); *C12N 2510/00* (2013.01); *Y02A 50/30* (2018.01)

(58) Field of Classification Search
CPC ........ A61K 35/44; A61K 35/28; A61K 39/42; A61K 39/12; C07K 16/10; G01N 33/6854; C12N 15/85
See application file for complete search history.

(56) References Cited

U.S. PATENT DOCUMENTS

| 7,101,704 | B1 | 9/2006 | Mosca |
| 8,076,102 | B2 | 12/2011 | Branco et al. |
| 9,101,597 | B2* | 8/2015 | Garry ..................... A61P 31/04 |
| 10,357,562 | B2* | 7/2019 | Garry .................. C12N 5/0667 |
| 2004/0039186 | A1 | 2/2004 | Tatake et al. |
| 2005/0053587 | A1 | 3/2005 | Galipeau et al. |
| 2005/0058983 | A1 | 5/2005 | Pinter et al. |
| 2007/0160585 | A1 | 7/2007 | Fujinaga et al. |
| 2007/0196365 | A1 | 8/2007 | Zipori et al. |
| 2008/0014205 | A1 | 1/2008 | Horowitz et al. |
| 2010/0226912 | A1 | 9/2010 | Mehtali |
| 2014/0178422 | A1 | 6/2014 | Tomchuck et al. |

FOREIGN PATENT DOCUMENTS

CA  2009129616 A1  10/2009

OTHER PUBLICATIONS

Abraham, E.J. et al., Human Pancreatic Islet-Derived Progenitor Cell Engraftment in Immunocompetent Mice, American Journal of Pathology, vol. 164 (3), 817-830 (2004).
Balyasnikova et al., J. Tissue Eng. Regen Med 4, 247-258 (2010).
Bao, C. et al., TNFR Gene-Modified Mesenchymal Stem Cells Attenuate Inflammation and Cardiac Dysfunction Following MI, Scandinavian Cardiovascular Journal 42, 56-62 (2008).
Bhargava, A. et al., Dendritic Cell Engineering for Tumor Immunotherapy: From Biology to Clinical Translation, Immunotherapy 4 (7), 703-718 (2012).
Cavenaugh, J.S. et al., Partially Randomized, Non-Blinded Trial of DNA and MVA Therapeutic Vaccines Based on Hepatitis B Virus Surface Protein for Chronic HBV Infection, PLoS One 6 (2), e14626 (2011).
Choi, J.J. et al., Mesenchymal Stem Cells Overexpressing Interleukin-10 Attenuate Collagen-Induced Arthritis in Mice, Clinical and Experimental Immunology 153, 269-276 (2008).
Compte, M. et al., Tumor Immunotherapy Using Gene-Modified Human Mesenchymal Stem Cells Loaded Into Synthetic Extracellular Matrix Scaffolds, Stem Cells, 27, 753-760 (2009).
Frank, R.T., et al., Concise Review: Stem Cells as an Emerging Platform for Antibody Therapy of Cancer, Stem Cells, 28, 2084-2087 (2010).
Gao, J. et al., The Dynamic In Vivo Distribution of Bone Marrow-Derived Mesenchymal Stem Cells After Infusion, Cells Tissues Organs 169, 12-20 (2001).

(Continued)

Primary Examiner — Scott Long
(74) Attorney, Agent, or Firm — Olson & Cepuritis, Ltd.

(57) ABSTRACT

Immunoprotective primary mesenchymal stems cells (IP-MSC) which episomally express immunoreactive polypeptides that specifically target a pathogen (e.g., an infectious species of virus, bacterium, or parasite) or toxin are described herein. The immunoreactive polypeptides can be, e.g., full antibodies, single-chain antibodies (ScFV), Fab or F(ab)$_2$ antibody fragments, diabodies, tribodies, and the like). Optionally IP-MSC are transfected to express one or more other immunomodulating polypeptides, e.g., a cytokine such as an interleukin (e.g., IL-2, IL-4, IL-6, IL-7, IL-9, and IL-12), an interferon (e.g., IFNα, IFNβ, or IFNω), and the like, which can enhance the effectiveness of the immunoreactive polypeptides.

20 Claims, 6 Drawing Sheets
Specification includes a Sequence Listing.

(56) References Cited

OTHER PUBLICATIONS

Hagiwara et al., Human Gene Therapy 19, 807-819 (2008).
Klinge, P.M. et al., Encapsulated Native and Glucagon-Like Peptide-1 Transfected Human Mesenchymal Stem Cells in a Transgenic Mouse Model of Alzheimer's Disease, Neuroscience Letters 497, 6-10 (2011).
Kumar, S., et al. Therapeutic Potential of Genetically Modified Adult Stem Cells for Osteopenia, Gene Therapy 17, 105-116 (2010).
Li, X. et al., In Vitro Effect of Adenovirus-Mediated Human Gamma Interferon Gene Transfer Into Human Mesenchymal Stem Cells for Chronic Myelogenous Leukemia, Hematological Oncology 24, 151-158 (2006).
Loebinger M.R. et al., Stem Cells as Vectors for Antitumour Therapy, Thorax 65, 362-369 (2010).
Logtenberg, T., Antibody Cocktails: Next Generation Biopharmaceuticals with Improved Potency, Trends in Biotechnology 25 (9), 390-394 (2007).
Ohtaki H. et al., Stem/Progenitor Cells From Bone Marrow Decrease Neuronal Death in Global Ischemia by Modulation of Inflammatory/Immune Responses, PNAS 105 (38), 14638-14643 (2008).
Palucka K. et al., Cancer Immunotherapy via Dendritic Cells, Nature Reviews/Cancer 12, 265-277 (2012).
Jayne, N.L., et al., Early Intervention With Gene-Modified Mesenchymal Stem Cells Overexpressing Interleukin-4 Enhances Anti-Inflammatory Responses and Functional Recovery in Experimental Autoimmune Demyelination, Cell Adhesion & Migration 6 (3), 179-189 (2012).
Porada, C.D. et al., Phenotypic Correction of Hemophilia A in Sheep by Postnatal Intraperitoneal Transplantation of FVIII-Expressing MSC, Exp. Hematol, 39 (12), 1124-1135 (2011).
Prockop D.J., Repair of Tissues by Adult Stem/Progenitor Cells (MSCs): Controversies, Myths, and Changing Paradigms, Molecular Therapy 17 (6), 939-946 (2009).
Ren, C. et al., Therapeutic Potential of Mesenchymal Stem Cells Producing IFN-α in a Mouse Melanoma Lung Metastasis Model, Stem Cells, vol. 26 (9), 2332-2338 (2008).
Sasaki, M. et al., BDNF-Hypersecreting Human Mesenchymal Stem Cells Promote Functional Recovery, Axonal Sprouting, and Protection of Corticospinal Neurons After Spinal Cord Injury, The Journal of Neuroscience 29 (47), 14932-14941 (2009).
Song, Y.S. et al., Mesenchymal Stem Cells Overexpressing Hepatocyte Growth Factor (HGF) Inhibit Collagen Deposit and Improve Bladder Function in Rat Model of Bladder Outlet Obstruction, Cell Transplantation 21, 1641-1650 (2012).
Stasi, A.D. et al., Inducible Apoptosis as a Safety Switch for Adoptive Cell Therapy, The New England Journal of Medicine 365, 1673-1683 (2011).
Tomchuck, S. L. et al., Mesenchymal Stem Cells as a Novel Vaccine Platform, Frontiers in Cellular and Infection Microbiology, vol. 2, (140) 1-7 (2012).
Vargas et al., Human Gene Therapy 15, 361-372 (2004).
Wang, Y. et al., Human Serum Amyloid P Functions as a Negative Regulator of the Innate and Adaptive Immune Responses to DNA Vaccines, The Journal of Immunology 186, 2860-2870 (2011).
Wei, H.J. et al., The Development of a Novel Cancer Immunotherapeutic Platform Using Tumor-Targeting Mesenchymal Stem Cells and a Protein Vaccine, Molecular Therapy, 1-8 (2011).
Wikipedia, Papillomaviridae, 1-17 (2018).
Yan, C. et al., Human Umbilical Cord Mesenchymal Stem Cells as Vehicles of CD20-Specific TRAIL Fusion Protein Delivery: A Double-Target Therapy Against Non-Hodgkin's Lymphoma, Molecular Pharmaceutics 10, 142-151 (2013).
Yu, J. et al., Human Induced Pluripotent Stem Cells Free of Vector and Transgene Sequences, Science 324, 797 (2009).

\* cited by examiner huMAb GP10.4B HC (SEQ ID NO: 1):

NTGCGCGTTACNGATCCAAGCTGTGACCGGCGCCTACCTGAGATCACCGGTGCTAGC
ACCATGGAGACAGACACACTCCTGCTATGGGTACTGCTGCTCTGGGTTCCAGGTTCC
ACTGGTGACCAGGTGCAGCTGGTACAGTCTGGGGGAGGCGTGGTCCAGCCTGGGAG
GTCCCTGAGAGTCTCCTGTGTTACGTCTGGATTCAATTTCAGAGCCTACGGCATGCAC
TGGGTCCGCCAGATTCCAGGCAAGGGACTGGAGTGGGTGGCAGATATTTGGTCTGCC
GAGACTAATAGACACTATGCAGATTCCGTGAAGGGCCGATTCACCATCTCCAGAGAC
AACTCCAAGAGCACACTGTATCTGCAAATGAACAGCCTGAGAGCCGAGGACACGGG
CGTATATTTCTGTGCCAAAGCGCGACCAGGCTATGATTATGTCGTTGACTTATGGGGC
CAGGGAACGCTGGTCATCGTCTCCTCAGCTTCCACCAAGGGCCCATCGGTCTTCCCCC
TGGCGCCCTGCTCCAGGAGCACCTCTGGGGGCACAGCGGCCCTGGGCTGCCTGGTCA
AGGACTACTTCCCCGAACCGGTGACGGTGTCGTGGAACTCAGGCGCCCTGACCAGCG
GCGTGCACACCTTCCCGGCTGTCCTACAGTCCTCAGGACTCTA huMAb GP 19.7E HC (SEQ ID NO: 2):

ATCCAGCTGTGACCGGCGCCTACCTGAGATCACCGGTGCTAGCACCATGGAGACAGA
CACACTCCTGCTATGGGTACTGCTGCTCTGGGTTCCAGGTTCCACTGGTGACGAGGTG
CAGCTGGTGGAGTCTGGGGGAGGCTTAGTTCGGCCTGGGGGGTCCCTGAGACTCTCC
TGTGCAGCCTCTGGATTCTCCTTCAGTAGCTACTCGATGCACTGGGTCCGCCATGTTC
CTGGGAAGGGGCTGGTGTGGGTCTCATATATTAATAGTGATGGGAGTACTAAAATCT
ACGCGGACTCCGTGAAGGGCCGATTCTCCATCTCCAGAGACAATGCCAAGAACAAGC
TCTATCTGCAAATGGACAGTTTGAGAGTCGAGGACACGGCTGTATATTCGTGTGTAA
GGCTTGTACATTACGACTGGTCCCCATTCGTGTGGGGCCAGGGAACCCTGGTCACCG
TCTCCTCAGCCTCCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCCGAACC
GGTGACGGTGTCGTGGAACTCAGGCGCCCTGACCAGCGGCGTGCACACCTTCCCGGC
TGTCCTACAGTCCTCAGGACTCTACTCCCTCAGCAGCGTGGTGACCGTGCCCTCCAGC
AGCTTGGGCACCCAGACCTACATCTGCAACGTGAATCACAAGCCCAGCAACACCAAG
GTGGACAAGAAAGTTGAGCCCCAATCTTGTGACAAAACTCACACATGCCCACCGTGC
CCAGCACCTGAACTCCT

FIG. 3 huMAb GP10.4B LC (SEQ ID NO: 3):

GCGCCGNTNNNATCCNAGCTGTGACCGGCGCCTACCTGAGATCACCGGTGCTAGCAC
CATGGAGACAGACACACTCCTGCTATGGGTACTGCTGCTCTGGGTTCCAGGTTCCACT
GGTGACGAAATTGTGTTGACACAGTCTCCATCCTCACTGTCTGCGTCTGTAGGAGACA
GAGTCACCATCACTTGTCGGGCGAGTCGGACATCAATACTTATTTAGGTTGGTTTCA
GCAGAGACCAGGGAAAGCCCCTAAGTCCCTGATCTATGGTGCATCTAATTTGCAAAA
TGGGGTCCCATCAAGGTTCAGCGGCAGTGGATCTGGGACGTATTTTACTCTCACCATC
AACGGCCTGCAGACTGAAGACTTTGCGACTTATTATTGCCAACAATATAGCATCTAC
CCGCTCAGTCTCGGCGGAGGGACCAAGGCGGACATGAAGCGAACTGTGGCTGCACC
ATCTGTCTTCATCTTCCCGCCATCTGATGAGCAGTTGAAATCTGGAACTGCCTCTGTT
GTGTGCCTGCTGAATAACTTCTATCCCAGAGAGGCCAAAGTACAGTGGAAGGTGGAT
AACGCCCTCCAATCGGGTAACTCCCAGGAGAGTGTCACAGAGCAGGACAGCAAGGA
CAGCACCTACAGCCTCAGCAGCACCCTGACGCTGAGCAAAGCAGACTACGAGAAAC
ACAAAGTCTACGCCTGCGAAGTCACCCATCAGGGCCTGAGCTCGCC huMAb GP19.7E LC (SEQ ID NO: 4):

CGTTCGATCCAGCTGTGACCGGCGCCTACCTGAGATCACCGGTGCTAGCACCATGGA
GACAGACACACTCCTGCTATGGGTACTGCTGCTCTGGGTTCCAGGTTCCACTGGTGAC
GATATTGTGATGACCCAGTCTCCTTCCACCCTGTCTGCATCTGTAGGAGACAGAGTCA
CCATCACTTGCCGGGCCAGTCAGAGTATTAATAATTGGTTGGCCTGGTATCAGGAGA
AACCAGGGAAAGCCCCTAAGCTCCTGATAAATAAGGCGTCTAGTTTAGAAAGTGGGG
TCCCATCAAGGTTCAGCGGCAGTGGATCTGGGACAGAATTCACTCTCACCATCACCA
GCCTGCAGCCTGATGATTTTGCAACTTATTACTGCCAACAATATAATAGTAATTCGTG
GACGTTCGGCCAAGGGACCAAGGTGGACATGAAACGAACTGTGGCTGCACCATCTGT
CTTCATCTTCCCGCCATCTGATGAGCAGTTGAAATCTGGAACTGCCTCTGTTGTGTGC
CTGCTGAATAACTTCTATCCCAGAGAGGCCAAAGTACAGTGGAAGGTGGATAACGCC
CTCCAATCGGGTAACTCCCAGGAGAGTGTCACAGAGCAGGACAGCAAGGACAGCAC
CTACAGCCTCAGCAGCACCCTGACGCTGAGCAAAGCAGACTACGAGAAACACAAAG
TCTACGCCTGCGAAGTCACCCATCAGGGCCTGAGCTCGCCCGTCACAAAGAGCTTCA
ACAGGGGAGAGTGTTAGAGGGAGCTAGCTCGACATGATAAGATACATTGATGAGTTT
GGACAAACCACAACTAGAATGCAGTGAAAAAATGCTTTATTTGTGAAATTTGTGAT
GCTATTGCTTTATTTGTGAAATTTGTGATGCTAT

FIG. 4 huMAb GP10.4B HC (SEQ ID NO: 5):

METDTLLLWVLLLWVPGSTGDQVQLVQSGGGVVQPGRSLRVSCVTSGFNFRAYGMHW
VRQIPGKGLEWVADIWSAETNRHYADSVKGRFTISRDNSKSTLYLQMNSLRAEDTGVYF
CAKARPGYDYVVDLWGQGTLVIVSSASTKGPSVFPLAPCSRSTSGGTAALGCLVKDYFP
EPVTVSWNSGALTSGVHTFPAVLQSSGLX huMAb GP19.7E HC (SEQ ID NO: 6):

METDTLLLWVLLLWVPGSTGDEVQLVESGGGLVRPGGSLRLSCAASGFSFSSYSMHWV
RHVPGKGLVWVSYINSDGSTKIYADSVKGRFSISRDNAKNKLYLQMDSLRVEDTAVYSC
VRLVHYDWSPFVWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDK
KVEPQSCDKTHTCPPCPAPEL huMAb GP10.4B LC (SEQ ID NO: 7):

METDTLLLWVLLLWVPGSTGDEIVLTQSPSSLSASVGDRVTITCRASRDINTYLGWFQQR
PGKAPKSLIYGASNLQNGVPSRFSGSGSGTYFTLTINGLQTEDFATYYCQQYSIYPLSLGG
GTKADMKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSS huMAb GP19.7E LC (SEQ ID NO: 8):

METDTLLLWVLLLWVPGSTGDDIVMTQSPSTLSASVGDRVTITCRASQSINNWLAWYQE
KPGKAPKLLINKASSLESGVPSRFSGSGSGTEFTLTITSLQPDDFATYYCQQYNSNSWTFG
QGTKVDMKRTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTKSFNRGEC

FIG. 5

IMMUNOPROTECTIVE PRIMARY MESENCHYMAL STEM CELLS AND METHODS

CROSS-REFERENCE TO RELATED APPLICATIONS

This application is a continuation of U.S. application Ser. No. 14/802,247, filed on Jul. 17, 2015, which is a continuation of U.S. application Ser. No. 13/826,285, filed on Mar. 14, 2013, now U.S. Pat. No. 9,101,587, each of which is incorporated herein by reference in its entirety.

FIELD OF THE INVENTION

This invention relates to mesenchymal stems cells. More particularly, this invention relates to primary mesenchymal stems cells (MSC) for delivery of polypeptides that are immunoreactive against pathological agents such as pathogens and toxins, as well as methods for preparation of such MSC and deployment of such MSC against pathological agents.

SEQUENCE LISTING INCORPORATION

Biological sequence information for this application is included in an ASCII text file having the file name "TU-491-SEQ.txt", created on Mar. 11, 2013, and having a file size of 12,954 bytes, which is incorporated herein by reference.

BACKGROUND

Mesenchymal stem cells (MSC) are unique multipotent progenitor cells that are presently being exploited as gene therapy vectors for a variety of conditions, including cancer and autoimmune diseases. Although MSC are predominantly known for anti-inflammatory properties during allogeneic MSC transplant, there is evidence that MSC can actually promote adaptive immunity under certain settings. MSC have been identified in a wide variety of tissues, including bone marrow, adipose tissue, placenta, and umbilical cord blood. Adipose tissue is one of the richest known sources of MSC.

MSC have been successfully transplanted into allogeneic hosts in a variety of clinical and pre-clinical settings. These donor MSC often promote immunotolerance, including the inhibition of graft-versus-host disease (GvHD) that can develop after cell or tissue transplantation from a major histocompatibility complex (MHC)-mismatched donor. The diminished GvHD symptoms after MSC transfer has been due to direct MSC inhibition of T and B cell proliferation, resting natural killer cell cytotoxicity, and dendritic cell (DC) maturation. At least one study has reported generation of antibodies against transplanted allogeneic MSC. Nevertheless, the ability to prevent GvHD also suggests that MSC expressing foreign antigen might have an advantage over other cell types (i.e., DC) during a cellular vaccination in selectively inducing immune responses to only the foreign antigen(s) expressed by MSC and not specifically the donor MSC.

The use of modified MSC also has been explored in vivo in order to enhance the immunomodulatory properties of MSC. MSC transduced to overproduce IL-10 suppressed collagen-induced arthritis in a mouse model (Choi et al., 2008). In addition, MSC expressing glucagon-like peptide-1 transplanted into an Alzheimer's disease mouse model led to a decrease in A-beta deposition in the brain (Klinge et al., 2011). In an osteopenia mouse model, mice receiving transduced MSC that had stable overexpression of bone morphogenetic protein had increased bone density (Kumar et al., 2010). In a rat model for spinal cord injury, rats treated with MSC stably overexpressing brain-derived neurotrophic factor had a better overall outcome than rats administered MSC alone (Sasaki et al., 2009). Lastly, in a rat model for bladder outlet obstruction, rats receiving transduced MSC with stable overexpression of hepatocyte growth factor had decreased collagen accumulation in the bladder (Song et al., 2012). These studies indicate that modified MSC are a useful and feasible vehicle for protein expression and delivery to target various diseases and tissues.

MSC have been studied as a delivery vehicle for anti-cancer therapeutics due to their innate tendency to home to tumor microenvironments, and is thoroughly reviewed in (Loebinger and Janes, 2010). MSC also have been used to promote apoptosis of tumorigenic cells through the expression of IFNα or IFNγ (Li et al., 2006; Ren et al., 2008). Additionally, MSC recently have been explored for the prevention and inhibition of tumorigenesis and metastasis. A study by Wei et al. examined the use of human papilloma virus (HPV)-immortalized MSC that express the HPV proteins E6/E7 combined with a modified E7 fusion protein vaccine in a mouse tumor model where metastatic fibrosarcoma cells were administered (Wei et al., 2011). This group found that only mice that were immunized with both the E7-expressing MSC and modified E7 protein vaccine showed a decrease in tumor growth, and an E7-specific antibody response. Mice receiving either MSC or protein vaccine alone were not able to raise an anti-E7 response or inhibit tumor growth of metastatic sarcoma. Although these immortalized MSC were previously determined to be non-tumorigenic, they persisted in mice longer than 21 days, unlike primary MSC (i.e. non-immortalized), which are only detectable for a very short time after administration (Gao et al., 2001; Abraham et al., 2004; Ohtaki et al., 2008; Prockop, 2009). Thus, there may be unforeseen outcomes in the long term (i.e., outcompeting with endogenous MSC and differing immunomodulatory abilities, which were not assessed in this study) with the use of immortalized MSC, even if they prove to be non-malignant. Other studies have indicated that immortalized MSC can become tumorigenic, and thus must be carefully studied to determine if they are indeed safe for use. Transplanted primary non-immortalized MSC persist only for a few days at most in vivo (Gao et al., 2001; Abraham et al., 2004; Ohtaki et al., 2008; Prockop, 2009).

While MSC are primarily touted for their immunosuppressive properties, several published reports have also directly shown that MSC promote adaptive immunity. In co-cultures, MSC enhanced B-cell proliferation, IL-6 expression and IgG-secreting plasma cell formation in vitro; these B-cell responses could be further augmented with MSC combined with a TLR agonist (lipopolysaccharide or CpG DNA). MSC pulsed with tetanus toxoid promoted the proliferation and cytokine expression (IL-4, IL-10, IFNγ) of a tetanus toxoid-specific CD4 T-cell line. Similarly, MSC cultured in low ratios (1:100) with lymphocytes in the presence of antigen improved lymphocyte proliferation and CD4 Th17 subset formation, which was partially IL-6 and TGFβ-dependent. MSC have also been found to express MHC-I and cross-present antigen for expansion of CD8 T-cells both in vitro and in vivo.

MSC immunoregulation has also been found to be dependent upon external signals. In the presence of inflammatory cytokines or stimulants, MSC therapy, which was previously suppressive, can become immunostimulatory. For example, MSC treated with specific pathogen-associated molecular pattern (PAMP) molecules can become either anti- or pro-inflammatory, depending on the PAMP with which they are treated in vitro. During collagen-induced arthritis, an inflammatory disease setting, transplantation of allogeneic MSC reportedly enhanced Th1 immune responses and IL-6 secretion, which was mimicked in vitro by direct TNFα stimulation of MSC. Administration of MSC also reportedly exacerbated collagen-induced arthritis disease and amplified splenocyte secretion of IL-6 and IL-17. Pre-treatment of MSC with IFNγ (within a moderate range) reportedly upregulates MHC-I and II expression and improves antigen phagocytosis and presentation capabilities, thereby stimulating CD4 and CD8 T-cell proliferation and generation of anti-tumor CD8+ cytotoxic T-lymphocytes (CTLs).

Vaccines often are efficient and cost-effective means of preventing infectious disease. Vaccines have demonstrated transformative potential in eradicating one devastating disease, smallpox, while offering the ability to control other diseases, including diphtheria, polio, and measles, that formerly caused widespread morbidity and mortality. The development of vaccines involves the testing of an attenuated or inactivated version of the pathogen or identification of a pathogen component (i.e., subunit, toxoid, and virus-like particle vaccines) that elicits an immune response that protects recipients from disease when they are exposed to the actual pathogen. In an ideal world a single vaccine would be able to target all major human pathogens (versatile), elicit strong protective immunity to these pathogens without inducing unwanted side-effects, and still be fairly inexpensive to produce per dose. In the case of viruses or host-cell produced proteins, vaccine production that includes human post-translational processing, mimicking natural infection, will likely prove to be superior to bacterial or other expression systems.

Traditional vaccine approaches have thus far failed to provide protection against HIV, tuberculosis, malaria and many other diseases, including dengue, herpes and even the common cold. The reasons why traditional vaccine approaches have not been successful for these diseases are complex and varied. For example, HIV integrates functional proviral genomes into the DNA of host cells, thereby establishing latency or persistence. Once latency/persistence is established, it has not been possible to eradicate HIV, even with highly active antiretroviral therapy.

Newer alternative immunization approaches include both DNA and cellular vaccines. DNA vaccines involve the transfection of cells at the tissue site of vaccination with an antigen-encoding plasmid that allows local cells (i.e. myocytes) to produce the vaccine antigen in situ. Cellular vaccines use the direct transfer of pre-pulsed or transfected host antigen presenting cells (e.g., dendritic cells, DC) expressing or presenting the vaccine antigen. The advantage of these approaches is that vaccine antigens are produced in vivo and are readily available for immunological processing. Despite numerous reports of successful pre-clinical testing, both such approaches have hit stumbling blocks. DNA vaccination studies in humans show poor efficacy, which has been linked to innate differences between mice and humans (Cavenaugh et al., 2011; Wang et al., 2011). DC vaccination strategies have shown limited clinical success for therapeutic cancer vaccinations and have high production costs due to necessary individual tailoring (Bhargava et al., 2012; Palucka and Banchereau, 2012).

A further limitation on current vaccine technology is the time involved in developing a vaccine against a give pathogen. This is particularly problematic in the case of exposure to newly emerging pathogens and deliberately or accidentally released pathogens and toxins, where the means for rapid protection to contain such emerging pathogens and biological threats are needed. The methods and episomally transfected MSC described herein address these needs.

SUMMARY OF THE INVENTION

The present invention provides immunoprotective primary mesenchymal stems cells (IP-MSC), which episomally express multiple immunoreactive polypeptides that specifically target a pathogen (e.g., an infectious species of virus, bacterium, or parasite) or a toxin, as well as methods of preparing and using the IP-MSC. The IP-MSC are transfected with one or more episomal vectors encoding two or more (e.g., 2 to about 100) expressible immunoreactive polypeptides (e.g., full antibodies, single chain variable antibodies fragments (ScFV), Fab or $F(ab')_2$ antibody fragments, diabodies, tribodies, and the like). Optionally, the IP-MSC can express one or more other immunomodulating polypeptides, e.g., a cytokine such as an interleukin (e.g., IL-2, IL-4, IL-6, IL-7, IL-9, and IL-12), an interferon (e.g., IFNα, IFNβ, or IFNω), and the like, which can enhance the effectiveness of the antigen-binding polypeptides to neutralize the pathogen or toxin. Each immunoreactive polypeptide comprises an amino acid sequence of an antigen-binding region from or of a neutralizing antibody (e.g., a native antibody from an exposed subject) specific for an antigen produced by the pathogen or specific for the toxin, or comprises an amino acid sequence of a variant of the antigen-binding region that includes one or more substitutions (e.g., conservative substitutions) in the amino acid sequence thereof, and preferably sharing at least about 50% sequence identity (e.g., at least about 60, 70, 80, 90, or 95% sequence identity) with the native antigen-binding region. Each antigen-binding region peptide or variant thereof is arranged and oriented to specifically bind to and neutralize the pathogen or toxin.

In some embodiments the IP-MSC express, e.g., at least 2, 3, 4, 5, or 6 immunoreactive polypeptides, or up to about 10, 20, 30, 40, 50, 60, 70, 80, 90 or 100 immunoreactive polypeptides, which specifically target the pathogen or toxin. For example, each immunoreactive polypeptide can specifically target and bind to a protein or fragment thereof from a pathogenic organism, or to a toxin (e.g., ricin, abrin, anthrax toxin, *botulinium* toxin), which can be produced by an organism in situ or may be encountered in a chemically isolated or purified form.

The IP-MSC are useful for generating passive immunity against or treating an infection by the pathogen or exposure to the toxin (e.g., by neutralization). The IP-MSC can be provided in a pharmaceutically acceptable carrier (e.g., a buffer, such as phosphate buffered saline, or any other buffered material suitable for sustaining viable transfected primary MSC) for use as a pharmaceutical composition for treating or preventing an infectious disease caused by the pathogen or ameliorating deleterious effects of a toxin. In some embodiments, the IP-MSC comprise bone-marrow derived MSC, while in some other embodiments, the IP-MSC comprise adipose MSC cells, placental MSC cells, or umbilical cord blood MSC cells.

The IP-MSC described herein are particularly useful for temporary passive protection against pathogens and toxins, at least in part, because primary MSC are hypo-immunogenic cells that generally are not targeted by the immune system. Thus, the IP-MSC are tolerated by the treated subject, allowing the cells to survive for a sufficient time for immunoreactive polypeptides to be expressed, produced, and released to bind to and neutralize a pathogenic organism or toxin to which the subject has been or may be exposed. In addition, primary MSC generally have a limited lifetime in the body, thus ameliorating potential for undesirable long-term side effects of treatment with the MSC (e.g., carcinogenicity), which may be an issue with immortalized MSC.

The following embodiments 1 to 35 of the present invention are provided to further illustrate the scope and various aspects of the invention. These embodiments are provided as non-limiting illustrations of the IP-MSC and methods described herein.

Embodiment 1 comprises immunoprotective primary mesenchymal stems cells (IP-MSC) that episomally express multiple immunoreactive polypeptides that specifically target a pathogen or toxin. The IP-MSC are transfected with one or more episomal vectors encoding the immunoreactive polypeptides. Each immunoreactive polypeptide comprises an amino acid sequence from an antigen-binding region of a neutralizing antibody specific for an antigen produced by the pathogen or specific for the toxin, or an amino acid sequence of a variant of the antigen-binding region sequence comprising one or more substitutions in the amino acid sequence thereof and sharing at least about 50% sequence identity with the sequence of the antigen-binding region; and the antigen-binding region sequence or variant thereof is arranged and oriented to specifically bind to and neutralize the pathogen or toxin; and wherein the episomal vector optionally includes an inducible apoptosis gene.

Embodiment 2 comprises the IP-MSC of embodiment 1 wherein the IP-MSC episomally express 2 to about 100 of the immunoreactive polypeptides.

Embodiment 3 comprises the IP-MSC of embodiment 1 or 2 wherein the IP-MSC also express one or more other immunomodulating agents.

Embodiment 4 comprises the IP-MSC of embodiment 3 wherein the one or more immunomodulating agents are selected from interleukins and interferons.

Embodiment 5 comprises the IP-MSC of embodiment 3 wherein the one or more immunomodulating agents are selected from IL-2, IL-4, IL-6, IL-7, IL-9, IL-12, IFNα, IFNβ, and IFNω.

Embodiment 6 comprises the IP-MSC of any one of embodiments 1 to 5 wherein each immunoreactive polypeptide is selected from a full-length antibody, a single-chain variable antibody fragment (ScFV), a monovalent antibody antigen-binding fragment (Fab), a divalent antibody antigen-binding fragment (F(ab')$_2$), a diabody, and a tribody.

Embodiment 7 comprises the IP-MSC of any one of embodiments 1 to 6 wherein one or more of the immunoreactive polypeptides comprises an amino acid sequence of the variant of the antigen-binding region, and wherein the amino acid sequence substitutions of the variant comprise conservative substitutions.

Embodiment 8 comprises the IP-MSC of any one of embodiments 1 to 7 wherein one or more of the immunoreactive polypeptides comprises an amino acid sequence of the variant of the antigen-binding region, and wherein the amino acid sequence of the variant shares at least about 80% sequence identity with the sequence of the antigen-binding region.

Embodiment 9 comprises the IP-MSC of any one of embodiments 1 to 8 wherein the pathogen is a viral pathogen.

Embodiment 10 comprises the IP-MSC of any one of embodiments 1 to 8 wherein the pathogen is a bacterial pathogen.

Embodiment 11 comprises the IP-MSC of any one of embodiments 1 to 8 wherein the pathogen is a single-celled parasitic pathogen.

Embodiment 12 comprises the IP-MSC of any one of embodiments 1 to 8 wherein the pathogen is a multicellular parasitic pathogen.

Embodiment 13 comprises the IP-MSC of any one of embodiments 1 to 8 wherein the pathogen is a viral pathogen selected from the group consisting of: an adenovirus; a papillomavirus; a hepadnavirus; a parvovirus; a pox virus; Epstein-Barr virus; cytomegalovirus (CMV); a herpes simplex virus; roseolovirus; varicella zoster virus; a filovirus; a paramyxovirus; an orthomyxovirus; a rhabdovirus; an arenavirus; a coronavirus; a human enterovirus; hepatitis A virus; a human rhinovirus; polio virus; a retrovirus; a rotavirus; a flavivirus; a hepacivirus; and rubella virus.

Embodiment 14 comprises the IP-MSC of any one of embodiments 1 to 8 wherein the pathogen is a bacterial pathogen from a genus selected from the group consisting of: *Bacillus*; *Bordetella*; *Borrelia*; *Brucella*; *Burkholderia*; *Campylobacter*; *Chlamydia*, *Chlamydophila*; *Clostridium*; *Corynebacterium*; *Enterococcus*; *Escherichia*; *Francisella*; *Haemophilus*; *Helicobacter*; *Legionella*; *Leptospira*; *Listeria*; *Mycobacterium*; *Mycoplasma*; *Neisseria*; *Pseudomonas*; *Rickettsia*; *Salmonella*; *Shigella*; *Staphylococcus*; *Streptococcus*; *Treponema*; *Vibrio*; and *Yersinia*.

Embodiment 15 comprises the IP-MSC of any one of embodiments 1 to 8 wherein the pathogen is a parasitic pathogen selected from the group consisting of: *Acanthamoeba*; *Anisakis*; *Ascaris lumbricoides*; *Balantidium coli*; *Cestoda* (tapeworm); Chiggers; *Cochliomyia hominivorax*; *Entamoeba histolytica*; *Fasciola hepatica*; *Giardia lamblia*; Hookworm; *Leishmania*; *Linguatula serrata*, Liver fluke; Loa loa; *Paragonimus* (lung fluke); Pinworm; *Plasmodium falciparum*; *Schistosoma*; *Strongyloides stercoralis*; Tapeworm; *Toxoplasma gondii*; *Trypanosoma*; Whipworm; and *Wuchereria bancrofti*.

Embodiment 16 comprises the IP-MSC of any one of embodiments 1 to 8 wherein the antigenic polypeptide is selected from the group consisting of: influenza hemagglutinin 1 (HA1); influenza hemagglutinin 2 (HA2); influenza neuraminidase (NA); Lassa virus (LASV) glycoprotein 1 (gp1); LASV glycoprotein 2 (gp2); LASV nucleocapsid-associated protein (NP); LASV L protein; LASV Z protein; SARS virus S protein; Ebola virus GP2; measles virus fusion 1 (F1) protein; HIV-1 transmembrane (TM) protein; HIV-1 glycoprotein 41 (gp41); HIV-1 glycoprotein 120 (gp120); hepatitis C virus (HCV) envelope glycoprotein 1 (E1); HCV envelope glycoprotein 2 (E2); HCV nucleocapsid protein (p22); West Nile virus (WNV) envelope glycoprotein (E); Japanese encephalitis virus (JEV) envelope glycoprotein (E); yellow fever virus (YFV) envelope glycoprotein (E); tick-borne encephalitis virus (TBEV) envelope glycoprotein (E); hepatitis G virus (HGV) envelope glycoprotein 1 (E1); respiratory synctival virus (RSV) fusion (F) protein; herpes simplex virus 1 (HSV-1) gD protein; HSV-1 gG protein; HSV-2 gD protein; HSV-2 gG protein; hepatitis B virus (HBV) core protein; Epstein-Barr virus (EBV) glycoprotein 125 (gp125); bacterial outer membrane protein assembly factor BamA; bacterial translocation assembly module protein TamA; bacterial polypeptide-transport associated protein domain protein; bacterial surface antigen D15; anthrax protective protein; anthrax lethal factor; anthrax edema factor; *Salmonella typhii* S1Da; *Sal-*

*monella typhii* S1Db; cholera toxin; cholera heat shock protein; *Clostridium botulinum* antigen S; *botulinum* toxin; *Yersina pestis* F1; *Yersina pestis* V antigen; *Yersina pestis* YopH; *Yersina pestis* YopM; *Yersina pestis* YopD; *Yersina pestis* plasminogen activation factor (Pla); *Plasmodium* circumsporozoite protein (CSP); *Plasmodium* sporozoite surface protein (SSP2/TRAP); *Plasmodium* liver stage antigen 1 (LSA1); *Plasmodium* exported protein 1 (EXP 1); *Plasmodium* erythrocyte binding antigen 175 (EBA-175); *Plasmodium* cysteine-rich protective antigen (cyRPA); *Plasmodium* heat shock protein 70 (hsp70); *Schistosoma* Sm29; and *Schistosoma* signal transduction protein 14-3-3.

Embodiment 17 comprises the IP-MSC of any one of embodiments 1 to 16 wherein the IP-MSC are prepared from bone marrow-derived mesenchymal stem cells.

Embodiment 18 comprises the IP-MSC of any one of embodiments 1 to 16 wherein the IP-MSC are prepared from adipose-derived mesenchymal stem cells.

Embodiment 19 comprises the IP-MSC of any one of embodiments 1 to 18 for treating an infection by the pathogen or toxicity from exposure to a toxin.

Embodiment 20 comprises the IP-MSC of any one of embodiments 1 to 18 for preventing an infection by the pathogen or preventing toxicity from exposure to the toxin.

Embodiment 21 comprises a pharmaceutical composition for treating an infection caused by the pathogen or treating exposure to the toxin comprising the IP-MSC of any one of embodiments 1 to 20 in a pharmaceutically acceptable carrier.

Embodiment 22 comprises a pharmaceutical composition for preventing an infection caused by the pathogen or for ameliorating the effects of exposure to the toxin comprising the IP-MSC of any one of embodiments 1 to 20 in a pharmaceutically acceptable carrier.

Embodiment 23 comprises use of the IP-MSC of any one of embodiments 1 to 20 for prevention of an infection caused by the pathogen or preventing toxicity from exposure to the toxin.

Embodiment 24 comprises use of the IP-MSC of any one of embodiments 1 to 20 for treating an ongoing infection caused by the pathogen or for ameliorating the effects of exposure to the toxin.

Embodiment 25 comprises use of the IP-MSC of any one of embodiments 1 to 20 for the manufacture of a pharmaceutical composition for treating an infection caused by the pathogen or for ameliorating the effects of exposure to the toxin.

Embodiment 26 comprises use of the IP-MSC of any one of embodiments 1 to 20 for the manufacture of a pharmaceutical composition for preventing an infection caused by the pathogen or preventing toxicity from exposure to the toxin.

Embodiment 27 comprises a method for treating an infection caused by the pathogen or treating exposure to the toxin comprising administering to a subject a therapeutically effective dosage of the IP-MSC of any one of embodiments 1 to 20.

Embodiment 28 comprises a method for preventing an infection caused by a pathogen or preventing toxicity from exposure to the toxin comprising administering to a subject a prophylactic dosage of the IP-MSC of any one of embodiments 1 to 20.

Embodiment 29 comprises a method for treating or preventing outbreak of a disease caused by a pathogen or ameliorating exposure to a toxin comprising the step of administering immunoprotective primary mesenchymal stem cells (IP-MSC) to a subject exposed to or at risk of being exposed to the pathogen or toxin; wherein the IP-MSC are transfected with one or more episomal vectors encoding at least two immunoreactive polypeptides, which specifically target the pathogen or toxin, each immunoreactive polypeptide comprising an antigen-binding region of a neutralizing antibody specific for the pathogen or toxin, or encoding a variant of the antigen-binding region, wherein the variant includes one or more substitutions in the amino acid sequence of the antigen-binding region and shares at least 50% sequence identity with the antigen-binding region of the neutralizing antibody.

Embodiment 30 comprises the method of embodiment 29 including the additional step of transfecting primary mesenchymal stem cells with one or more episomal vectors encoding the at least two immunoreactive polypeptides.

Embodiment 31 comprises the method of embodiment 30 including the additional step of identifying neutralizing antibodies to the pathogen or toxin from one or more blood samples obtained from one or more survivors of the pathogenic disease or toxin exposure, prior to transfecting the primary MSC.

Embodiment 32 comprises the method of any one of embodiments 29 to 31 including the additional step of preparing one or more episomal vectors encoding expressible amino acid sequences of the at least two or more immunoreactive polypeptides prior to transfecting the primary MSC.

Embodiment 33 comprises the method of any one of embodiments 29 to 32 wherein the IP-MSC are selected from any one of embodiments 1 to 20.

Embodiment 34 comprises a method for preparing prophylactic or therapeutic mesenchymal stem cells for treating or preventing an outbreak of a disease caused by a pathogen or for ameliorating exposure to a toxin comprising the step of transfecting primary mesenchymal stem cells with one or more episomal vectors encoding at least two immunoreactive polypeptides comprising an amino acid from an antigen-binding region of a neutralizing antibody specific for the pathogen or toxin, or encoding a variant of the antigen-binding region sequence, to produce immunoprotective primary mesenchymal stem cells (IP-MSC) that express the immunoreactive polypeptides; wherein the variant includes one or more substitutions in the amino acid sequence from the antigen-binding region and shares at least 50% sequence identity with the antigen-binding region sequence of the neutralizing antibody.

Embodiment 35 comprises the method of embodiment 34 including the additional step of identifying neutralizing antibodies to the pathogen or toxin from a blood sample obtained from one or more survivors of the pathogenic disease or toxin exposure prior to transfecting the primary MSC.

Embodiment 36 comprises the method of embodiment 34 or embodiment 35 including the additional step of preparing one or more episomal vectors encoding expressible amino acid sequences of the at least two or more immunoreactive polypeptides prior to transfecting the primary MSC.

Embodiment 37 comprises the method of any one of embodiments 34 to 36 wherein the IP-MSC are selected from any one of embodiments 1 to 20.

Embodiment 38 comprises an episomal vector encoding an expressible amino acid sequence of an immunoprotective polypeptide; wherein each immunoreactive polypeptide comprises an amino acid sequence from an antigen-binding region of a neutralizing antibody specific for an antigen produced by the pathogen or specific for the toxin, or an amino acid sequence of a variant of the antigen-binding region sequence comprising one or more substitutions in the amino acid sequence thereof and sharing at least about 50% sequence identity with the antigen-binding region sequence; the antigen-binding region sequence or variant thereof being arranged to specifically bind to and neutralize the pathogen or toxin; and wherein the episomal vector optionally includes an inducible apoptosis gene.

BRIEF DESCRIPTION OF THE DRAWINGS

FIG. 3 illustrates nucleotide sequences of the heavy chains of human anti-LASV IgG MAb GP10.4B (SEQ ID NO: 1) and human anti-LASV MAb GP19.7E (SEQ ID NO: 1).

FIG. 4 illustrates nucleotide sequences of the light chains of human anti-LASV IgG MAb GP10.4B (SEQ ID NO: 3) and human anti-LASV MAb GP19.7E (SEQ ID NO: 4).

FIG. 5 illustrates amino acid sequences of the heavy and light chains of human anti-LASV IgG MAb GP10.4B (HC: SEQ ID NO: 5; LC: SEQ ID NO: 7) and human anti-LASV MAb GP19.7E (HC: SEQ ID NO: 6; LC: SEQ ID NO: 8).

DETAILED DESCRIPTION OF SELECTED EMBODIMENTS

Figure 1:
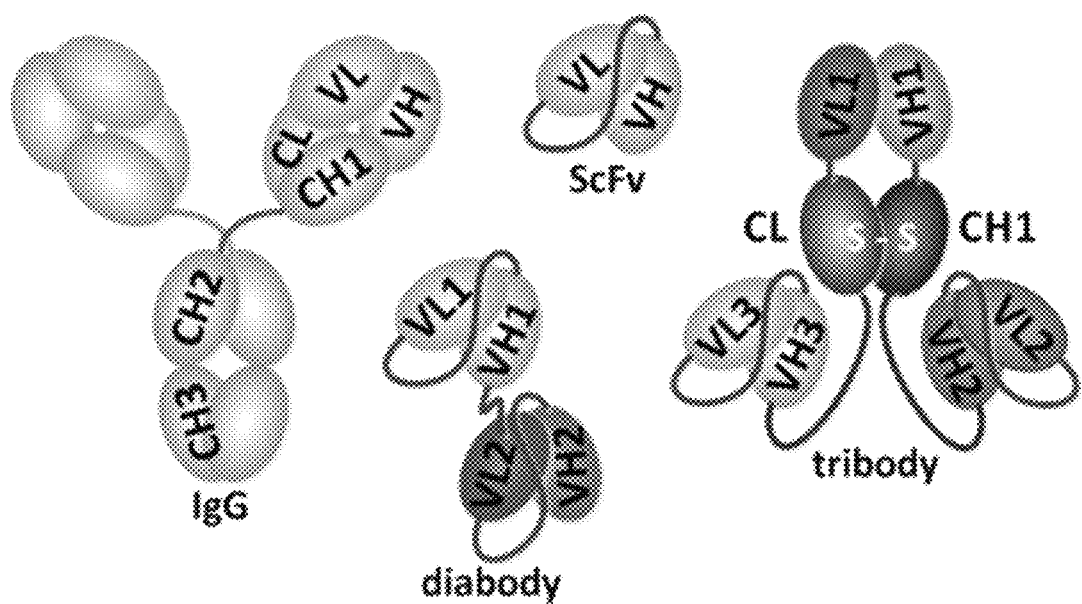
FIG. 1 provides a schematic illustration of a full-length IgG antibody, a ScFV, a tandem diabody, and a tribody.

Immunoprotective primary mesenchymal stems cells described herein episomally express multiple immunoreactive polypeptides that specifically target a pathogen or toxin of interest. Each immunoreactive polypeptide comprises an amino acid sequence of an antigen-binding region of a neutralizing antibody specific for an antigen produced by the pathogen or specific for the toxin, or an amino acid sequence of a variant of the antigen-binding region comprising one or more substitutions in the amino acid sequence thereof and sharing at least about 50% sequence identity with the antigen-binding region. The antigen-binding region or variant thereof is arranged and oriented to specifically bind to and neutralize the pathogen or toxin, i.e., when the IP-MSC are contacted with the pathogen or toxin, for example when the IP-MSC are administered to a subject and the subject is exposed to the pathogen or toxin. The substitutions in the variant can comprise or consist of conservative substitutions, or in some cases non-conservative substitutions that enhance the binding affinity or binding selectivity of the variant relative to the native antigen-binding region, or which improve, enhance or otherwise desirably affect one or more properties of the immunoreactive polypeptides, such as a physical, chemical, or conformational property.

The IP-MSC potentially can be utilized against any pathogen or toxin for which neutralizing antibodies can be identified. The IP-MSC and methods described herein are particularly useful for providing a relatively rapidly deployable, but short-term (e.g., up to one or two months) passive immunity against a pathogen or toxin. Such pathogens include viruses, bacteria, parasites (single cell and multicellular parasites), and the like. For example, the IP-MSC can be utilized as a protective agent in the case of a deliberate or accidental release of a pathogen or toxin. In addition, IP-MSC against particular pathogenic viruses (e.g., LASV, Ebola virus, Dengue virus), bacteria (*Rickettsia typhi, Neisseria meningitidis, Borrelia* spp., *Vibrio cholerae*, and the like) or parasites (e.g., *Plasmodium, Trypanosoma, Leishmania, Schistosoma*, and the like) can be utilized as a temporary protection for subjects traveling to areas where the pathogens are endemic, or for prevention of infections commonly acquired by patients in hospitals (e.g., Methicillin-Resistant *Staphylococcus Aureus, Psuedomonas Aeruginosa*, Vancomycin-Resistant *Enterococci, Streptococcus pneumoniae*, and the like).

An important contributing factor to therapeutics designed around MSC is the ease of MSC isolation and expansion in culture. Theoretically, a single bone marrow harvest of MSC may yield sufficient MSC for thousands of clinical applications, due to their inherent expansion capability (Newman et al., 2009). Such expansion potential greatly enhances the GMP manufacturing capability of using MSC for clinical applications and has lower production costs when compared to other cell types.

As used herein, the term "immunoreactive polypeptide" and grammatical variations thereof refers to a polypeptide that includes a peptide encoding an antigen-binding region of a neutralizing antibody to the pathogen or toxin of interest, or a variant of the antigen-binding region which retains specificity for the pathogen or toxin, but differs from a native antibody structure by the presence of one or more substitution (e.g., a conservative substitution) in the amino acid sequence of the native antigen-binding region. Non-limiting examples of immunoreactive polypeptides include full length antibodies (e.g., an IgG antibody), antigen-binding fragments of such full length antibodies, and other polypeptides that include one or more complementarity determining region (CDR) of such antibodies arranged and oriented to bind to an antigen. Functional antigen-binding antibody fragments include Fab, F(ab')$_2$, Fv, ScFv, diabody, and tribody polypeptides.

As used herein, the term "antigen-binding region" refers to the site of an antibody that binds to an antigen. The antigen-binding region is comprised of heavy chain and light chain variable domains ($V_H$ and $V_L$), each of which includes four conserved framework regions (FR) and three CDRs. The CDRs vary in sequence and determine the specificity of the antibody to a particular antigen. The $V_H$ and $V_L$ domains together form the site that specifically binds a particular antigen.

Fab (fragment antigen binding) antibody fragments are immunoreactive polypeptides comprising monovalent antigen-binding domains of an antibody composed of a polypeptide consisting of a heavy chain variable region ($V_H$) and heavy chain constant region 1 ($C_H1$) portion and a polypeptide consisting of a light chain variable ($V_L$) and light chain constant ($C_L$) portion, in which the $C_L$ and $C_H1$ portions are bound together, preferably by a disulfide bond between Cys residues.

A $F_V$ antibody fragment is a dimer that contains the $V_H$ and $V_L$ domains.

A F(ab')$_2$ fragment is composed of two Fab-type polypeptides bound together by a disulfide bridge between the $C_H1$ portions thereof.

A ScFV ("single chain fragment variable" or "single chain antibody") is an immunoreactive polypeptide comprising $V_L$ and $V_H$ peptides joined together by a flexible, generally hydrophilic linking peptide, of sufficient length (generally about 15 amino acids in length) to allow the $V_L$ and $V_H$ to associate in an antigen-binding configuration. One common flexible linking peptide is $(Gly_4Ser)_3$. Optionally, the association of the $V_H$ and $V_L$ can be stabilized by one or more intermolecular disulfide bonds.

As used herein and as commonly understood in the art, the term "diabody" refers to an immunoreactive polypeptide comprising either (a) two ScFV linked together by a short peptide or bond between two ScFV (e.g., between the $V_L$ portions) to form a tandem dimeric ScFV or (b) a complex comprising two ScFV-like polypeptides in which the linking peptide is too short to allow direct interaction between the $V_L$ and $V_H$ of the same polypeptide chain so that two such molecules are forced to associate intermolecularly as a dimer. The two antigen-binding domains of the diabody can be specific for the same antigen or two different antigens.

As used herein and as commonly understood in the art, the term "tribody" refers to an immunoreactive polypeptide comprising three ScFV-like antigen binding domains. Structurally, a tribody is a dimer composed of two polypeptide chains bound together by a disulfide bridge, in which the first polypeptide comprises an ScFV linked to an additional $V_L$ domain through a $C_L$ polypeptide chain, and the second polypeptide comprises an ScFV linked to an additional $V_H$ domain through a $C_H1$ polypeptide chain. The disulfide bridge is formed between a Cys residue in the $C_L$ and a Cys residue in the $C_H1$, such that the additional $V_L$ of the first polypeptide associates with the additional $V_H$ of the second polypeptide in an antigen-binding configuration, such that the tribody as a whole includes three antigen-binding domains. The three antigen-binding domains of the tribody can be specific for the same antigen or two or three different antigens.

FIG. 1 schematically illustrates a full length IgG antibody, an ScFV, a tandem-type diabody, and a tribody as discussed above.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferably, the immunoprotective polypeptides share at least about 50% sequence identity with the antigen-binding region of a naturally occurring (native) antibody (e.g., at least about 55, 60, 65, 70, 75, 80, 85, 90, 95, 98, or 99% sequence identity with the naturally occurring antibody antigen-binding region). As used herein, the terms "naturally occurring antibody", "native antibody" and grammatical variations thereof refer to an antibody specific for the pathogen or toxin of interest, which is identified from a blood sample of a subject exposed to the pathogen or toxin.

Non-limiting examples of viral pathogens that can be targeted by the immunoprotective polypeptides produced by the IP-MSC described herein include: adenoviruses; papillomaviruses; hepadnaviruses (e.g., hepatitis B); parvoviruses; pox viruses (e.g., small pox virus, vaccinia virus); Epstein-Barr virus; cytomegalovirus (CMV); herpes simplex viruses; roseolovirus; varicella zoster virus; filoviruses (e.g., Ebola virus and Marburg virus); paramyxoviruses (e.g., measles virus, mumps virus, Nipah virus, Hendra virus, human respiratory syncytial virus (RSV), parainfluenza viruses, Newcastle disease virus, and human metapneumovirus); orthomyxoviruses (e.g., influenza A, influenza B, and influenza C); rhabdoviruses (e.g., Lyssavirus, also known as rabies virus); arenaviruses (e.g., Lassa virus); coronaviruses (severe acute respiratory syndrome (SARS)); human enteroviruses; hepatitis A virus; human rhinoviruses; polio virus; retroviruses (e.g., human immunodeficiency virus 1(HIV-1)); rotaviruses; flaviviruses, (e.g., West Nile virus, dengue virus, yellow fever virus); hepaciviruses (e.g., hepatitis C virus); and rubella virus.

Non-limiting examples of bacterial pathogens that can be targeted by the immunoprotective polypeptides produced by the IP-MSC described herein include any pathogenic bacterial species from a genus selected from: *Bacillus; Bordetella; Borrelia; Brucella; Burkholderia; Campylobacter; Chlamydia, Chlamydophila; Clostridium; Corynebacterium; Enterococcus; Escherichia; Francisella; Haemophilus; Helicobacter; Legionella; Leptospira; Listeria; Mycobacterium; Mycoplasma; Neisseria; Pseudomonas; Rickettsia; Salmonella; Shigella; Staphylococcus; Streptococcus; Treponema; Vibrio;* and *Yersinia.*

Non-limiting examples of parasitic pathogens that can be targeted by the immunoprotective polypeptides produced by the IP-MSC described herein include single cell and multicellular parasites, such as: *Acanthamoeba; Anisakis; Ascaris lumbricoides; Balantidium coli; Cestoda* (tapeworm); Chiggers; *Cochliomyia hominivorax; Entamoeba histolytica; Fasciola hepatica; Giardia lamblia;* Hookworm; *Leishmania; Linguatula serrata;* Liver fluke; Loa loa; *Paragonimus* (lung fluke); Pinworm; *Plasmodium falciparum; Schistosoma; Strongyloides stercoralis,* Tapeworm, *Toxoplasma gondii; Trypanosoma;* Whipworm; and *Wuchereria bancrofti.*

Non-limiting examples of viral antigens that can be targeted by the immunoprotective polypeptides produced by the IP-MSC described herein include: influenza polypeptides such as hemagglutinin 1 (HA1), hemagglutinin 2 (HA2), and neuraminidase (NA); Lassa virus (LASV) polypeptides such as LASV glycoprotein 1 (gp1), LASV glycoprotein 2 (gp2), LASV nucleocapsid-associated protein (NP), LASV L protein, and LASV Z protein; SARS virus polypeptides such as SARS virus S protein; Ebola virus polypeptides such as Ebola virus GP2; measles virus polypeptides such as measles virus fusion 1 (F1) protein; HIV-1 polypeptides such as HIV transmembrane (TM) protein, HIV glycoprotein 41 (gp41), HIV glycoprotein 120 (gp120); hepatitis C virus (HCV) polypeptides such as HCV envelope glycoprotein 1 (E1), HCV envelope glycoprotein 2 (E2), HCV nucleocapsid protein (p22); West Nile virus (WNV) polypeptides such as WNV envelope glycoprotein (E); Japanese encephalitis virus (JEV) polypeptides such as JEV envelope glycoprotein (E); yellow fever virus (YFV) polypeptides such as YFV envelope glycoprotein (E); tick-borne encephalitis virus (TBEV) polypeptides such as TBEV envelope glycoprotein (E); hepatitis G virus (HGV) polypeptides such as HGV envelope glycoprotein 1 (E1); respiratory synctival virus (RSV) polypeptides such as RSV fusion (F) protein; herpes simplex virus (HSV) polypeptides such as HSV-1 gD protein, HSV-1 gG protein, HSV-2 gD protein, and HSV-2 gG protein; hepatitis B virus (HBV) polypeptides such as HBV core protein; and Epstein-Barr virus (EBV) polypeptides such as EBV glycoprotein 125 (gp125).

Non-limiting examples of bacterial antigens that can be targeted by the immunoprotective polypeptides produced by the IP-MSC described herein include: outer membrane protein assembly factor BamA; translocation assembly module protein TamA; polypeptide-transport associated protein domain protein; bacterial surface antigen D15 from a wide variety of bacterial species; *Bacillus anthracis* polypeptides such as anthrax protective protein, anthrax lethal factor, and anthrax edema factor; *Salmonella typhii* polypeptides such as S1Da and S1Db; *Vibrio cholerae* polypeptides such as cholera toxin and cholera heat shock protein; *Clostridium botulinum* polypeptides such as antigen S and *botulinum* toxin; and *Yersina pestis* polypeptides such as F1, V antigen, YopH, YopM, YopD, and plasminogen activation factor (Pla).

Non-limiting examples of parasite antigens that can be targeted by the immunoprotective polypeptides produced by the IP-MSC described herein include: malarial (*Plasmodium*) polypeptides such as circumsporozoite protein (CSP), sporozoite surface protein (SSP2/TRAP), liver stage antigen 1 (LSA1), exported protein 1 (EXP 1), erythrocyte binding antigen 175 (EBA-175), cysteine-rich protective antigen (cyRPA), and *Plasmodium* heat shock protein 70 (hsp70); and *Schistosoma* polypeptides such as Sm29 and signal transduction protein 14-3-3.

Preferably, the IP-MSC are administered parenterally (e.g. intravenous, subcutaneous, or intramuscular injection or infusion). The IP-MSC can be formulated as a solution, suspension, or emulsion in association with a pharmaceutically acceptable carrier vehicle (e.g., sterile water, saline, dextrose solution, phosphate buffered saline, and similar materials suitable for administration of live stem cells). Optionally, additives that maintain isotonicity (e.g. mannitol) or chemical stability (e.g. preservatives) can be included in the carrier.

As used herein, a "therapeutically effective dosage" is an amount (e.g., number of IP-MSC) such that when administered, the IP-MSC result in a reduction or elimination of already present disease symptoms (e.g., about one hundred thousand to about one hundred million cells). The dosage and number of doses (e.g. single or multiple dose) administered to a subject will vary depending upon a variety of factors, including the route of administration, patient conditions and characteristics (sex, age, body weight, health, size), extent of symptoms, concurrent treatments, frequency of treatment and the effect desired, the identity and number of antigenic polypeptides expressed by the IP-MSC, and the like. Adjustment and manipulation of established dosage ranges, as well as in vitro and in vivo methods of determining the therapeutic effectiveness of the IP-MSC in an individual, are well within the ability of those of ordinary skill in the medical arts.

A "prophylactic dosage" is an amount (e.g., number of IP-MSC) such that when administered, the MSC prevent infection by the pathogen from which the polypeptide expressed by the IP-MSC was derived (e.g., about one hundred thousand to about one hundred million cells). The dosage and number of doses (e.g. single or multiple dose) administered to a subject will vary depending upon a variety of factors, including the route of administration, patient conditions and characteristics (sex, age, body weight, health, size), extent of symptoms, concurrent treatments, frequency of treatment and the effect desired, the identity and number of antigenic polypeptides expressed by the IP-MSC, and the like. Adjustment and manipulation of established dosage ranges, as well as in vitro and in vivo methods of determining the prophylactic effectiveness of the IP-MSC in an individual, are well within the ability of those of ordinary skill in the medical arts.

As used herein, the term "episomally transfected" and grammatical variations thereof refer to non-integrating transfection with exogenous episomal DNA (e.g. a plasmid or other episomal vector) to produce a cell with unaltered chromosomal DNA, in which the polypeptide encoded by the DNA is expressed in an episome within the MSC, i.e., without genomic integration of the exogenous DNA. As used herein, the term "episome" and grammatical variations thereof refers to closed circular DNA molecules that are replicated in the nucleus, and is intended to encompass exogenous plasmids introduced into the MSC. Preferably, primary MSC are transfected with a plasmid that encodes the antigenic polypeptide, and preferably also encodes regulatory elements (e.g., a promoter) to facilitate episomal expression of the antigenic polypeptide. Optionally, the also MSC can be episomally transfected with an inducible apoptosis gene to induce cell death (apoptosis) when activated by a suitable signal (e.g., using Tetracycline-Controlled Transcriptional Activation, also referred to as "Tet-on and Tet-off", in which tetracycline or doxycycline is used to turn on transcription of the apoptotic gene), so that the IP-MSC can be eliminated from the subject if desired or needed (e.g., if undesired side-affects develop). The term "episomal vector" refers to an expression vector comprising a plasmid or other circular DNA encoding the antigenic polypeptide.

Primary MSC can be episomally transfected by any suitable methodology. For example, the Primary MSC can be transfected with a plasmid encoding the antigenic polypeptide using electroporation, lipofection, and the like. Electroporation is the preferred method for transfection, unlike other transfection approaches using cationic lipids (i.e. lipofection) as there may be residual lipids after transfection that may not be completely removed when processing the MSC for delivery, and may result in unforeseen side effects.

Non limiting examples of episomal vectors suitable for use as non-integrating vectors for transfection of eukaryotic cells (e.g., primary MSC) include simian virus 40-based vectors, Epstein-Barr virus-based vectors, papilloma virus-based vectors, BK virus-based vectors, and the like, which are well known in the molecular genetics art.

Also described herein is a method for treating or preventing a pathogenic disease or ameliorating exposure to a toxin, utilizing the IP-MSC described herein. One method embodiment comprises the steps of: optionally identifying neutralizing antibodies to the pathogen or toxin identified from a blood sample from one or more survivors of the pathogenic disease or toxin exposure; transfecting primary mesenchymal stem cells with one or more episomal vectors encoding at least two immunoreactive polypeptides comprising an antigen-binding region of a neutralizing antibody specific for the pathogen or toxin (e.g., an antibody identified in step (a)), or encoding a variant of the antigen-binding region, to produce IP-MSC that express the immunoreactive polypeptides; and administering the IP-MSC to a subject exposed to or at risk of being exposed to the pathogen or toxin. The variant, if utilized, includes one or more substitutions in the amino acid sequence of the antigen-binding region preferably shares at least 50% sequence identity with the antigen-binding region of the neutralizing antibody.

Selection and Design of Antibodies and Immune Molecules.

Advanced methods for transport of immune cells from survivors of exposure to pathogenic agents or toxins. Isolation and cryopreservation of peripheral blood mononuclear cells (PBMC) from blood samples should preserve the integrity of as many B cells as is practical, to ensure eventual recovery and characterization of abundant and rare specificities. As proof of concept, convalescent Lassa fever (LF) patients at West African clinical research sites (Kenema Government Hospital, Sierra Leone and Irrua Specialist Teaching Hospital, Nigeria) are identified using modern recombinant protein-based immunodiagnostics. Whole blood is drawn after fully informed consent, and PBMC are isolated in dedicated and fully equipped cell culture suites. PBMC are cryopreserved using established buffers (RPMI/20% FBSΔ/10% DMSO) and methods (cooling rate of about −1° C./min to a final temperature of about −80° C., >5×10$^6$ cells/vial) that generate highly viable cell cultures after thawing. Samples are rapidly transported to the U.S. in IATA-approved cryogenic containers for further processing. The number and percentage of B cells prior to cryopreservation are assessed onsite by quantitative flow cytometry (with the aid of a highly portable BD ACCURIC6 cytometer), by determining total number of PBMC, and specifically B cells (CD19+, CD20+), T cells (CD3+, CD 4+, CD 8+), NK cells (CD16+, CD 56+), and monocytes (CD14+, CD 16+) from each isolation procedure. The procedure is repeated upon thawing to determine loss rates of PBMC and cell subsets. Similar procedures can be employed in identifying other antibodies, e.g., influenza antibodies, produced by PBMC from subjects with documented recent infections. Where appropriate, as in influenza, cryopreservation might be bypassed, permitting isolation of B cells from fresh blood draws.

Methodology for rapid determination of the microbiome in an index patient convalescing from a pathogen or toxin. To demonstrate that the MSC gene delivery platform can be deployed rapidly as a firebreak for a high-risk group (warfighters, first responders, etc.) against a highly transmissible disease a novel pathogen identified in Sierra Leone or Nigeria is used as a model. This closely replicates or simulates the scenario of a patient accessible about 2 to 3 weeks following exposure to a pathogen or toxin (e.g., of known or unknown origin), as well as deliberately-released or accidentally-released pathogens or toxins.

Microbial metagenomics, the unbiased characterization of microbial nucleic acids, can rapidly identify infectious pathogens in patients convalescing from unknown biothreats. Microbes present in clinical samples are typically identified by culture or by targeted molecular approaches, such as PCR or antigen capture. Culturing is time-consuming and many microbes simply cannot be cultured in vitro. Targeted approaches are also disadvantageous because they require a priori knowledge of the organism. About 30% of microbial reads in fever of unknown origin (FUO) samples from Sierra Leone and Nigeria have no match in the GENBANK database. The technology described herein is sensitive (i.e., able to detect a low-copy pathogen in a diverse mixture of endogenous microbes) and scalable (i.e., able to survey large numbers of patient samples quickly). Improved molecular methods for constructing Illumina sequencing libraries are developed using sub-nanogram quantities of RNA. Current library construction methods are scaled up so that hundreds of samples can be processed in parallel. A bioinformatics pipeline is developed that can rapidly identify all microbes present in massive next-generation sequencing data sets. With these methods in place, a complete genome is assembled from an unknown virus within about 2 days and an unknown bacterium within about 4 days.

Computer programs for identifying pathogen virulence determinants (e.g. viral entry glycoproteins or toxins). Virulence factors refer to the proteins (i.e., gene products) that enable a microorganism to establish itself in humans and enhance its potential to cause disease. A bioinformatics and computational pipeline that can rapidly identify virulence factors of previously unknown organisms from large metagenomic datasets is developed that leverages several publicly available virulence factor databases (MvirDB, ToxProt, SCORPION, the PRINTS virulence factors, VFDB, TVFac, Islander, ARGO and a subset of VIDA) and enables rapid (within a few hours) identification of virulence factors for newly completed genomic sequence data. Experiments are performed to confirm the ability of the program to correctly identify virulence factors that can be targeted for protective antibodies.

Protective antibodies. B cells are enriched by depletion of non-B cells from PBMC using a MACS separator (Miltenyi Biotec) and magnetic beads coated with, e.g., αCD2, CD4, CD11b, CD16, CD36, αIgE, CD235a, and the like. Antigen-specific circulating memory B cells that bind to fluorochrome-labeled recombinant virulence determinants (e.g. LASV GP or influenza virus hemagglutinin, HA) are sorted by flow cytometry and directly deposited in 96 well plates at single cell densities. RNA is isolated from single cells (Norgen Biotek, Qiagen) and reverse transcribed into cDNA, with subsequent amplification of immunoglobulin heavy and light chains. Custom designed oligos permit direct cloning of heavy and light chain genes into proprietary vectors for expression as complete human monoclonal antibodies (CHOLCelect™, U.S. Pat. No. 8,076,102, Luis M Branco et al., which is incorporated herein by reference in its entirety), or re-engineered as single chain, diabodies, or tribodies for rapid expression and purification from E. coli cultures. ELISAs for binding to virulence determinants (GP or HA) or pathogen neutralization (pseudoparticle-based) assays are used to rapidly identify potentially protective antibodies. Antibodies with desired properties are cloned in the polyclonal expression vector described herein, and are tested as single specificities in live virus neutralization assays to verify potency in a more relevant in vitro biological system.

Methods for avoiding formation of chimeric improperly assorted antibodies. To ensure the development of the most widely applicable, protective, and escape mutant-resistant platform an oligoclonal antibody design is implemented. To this end each antibody displaying neutralizing properties desirably is tested as full length and single chain (ScFV) versions. Many ScFV preserve the properties of parent whole IgGs due to faithful representation of crucial antigen-binding CDRs. Alternatively, diabody and tribody combinations can be incorporated in expression vector platforms for therapeutic use. This IgG/ScFV oligoclonal approach will prevent formation of inappropriately mixed heavy and light chains when more than one antibody is expressed within a single MSC. In some embodiments, a desired level of therapeutic potency is achieved by integrating several ScFVs and one full length antibody for which effector functions may be identified or that lost potency upon conversion to a single chain variant.

Selection and Design of Nucleic Acid Constructs.

Figure 2:
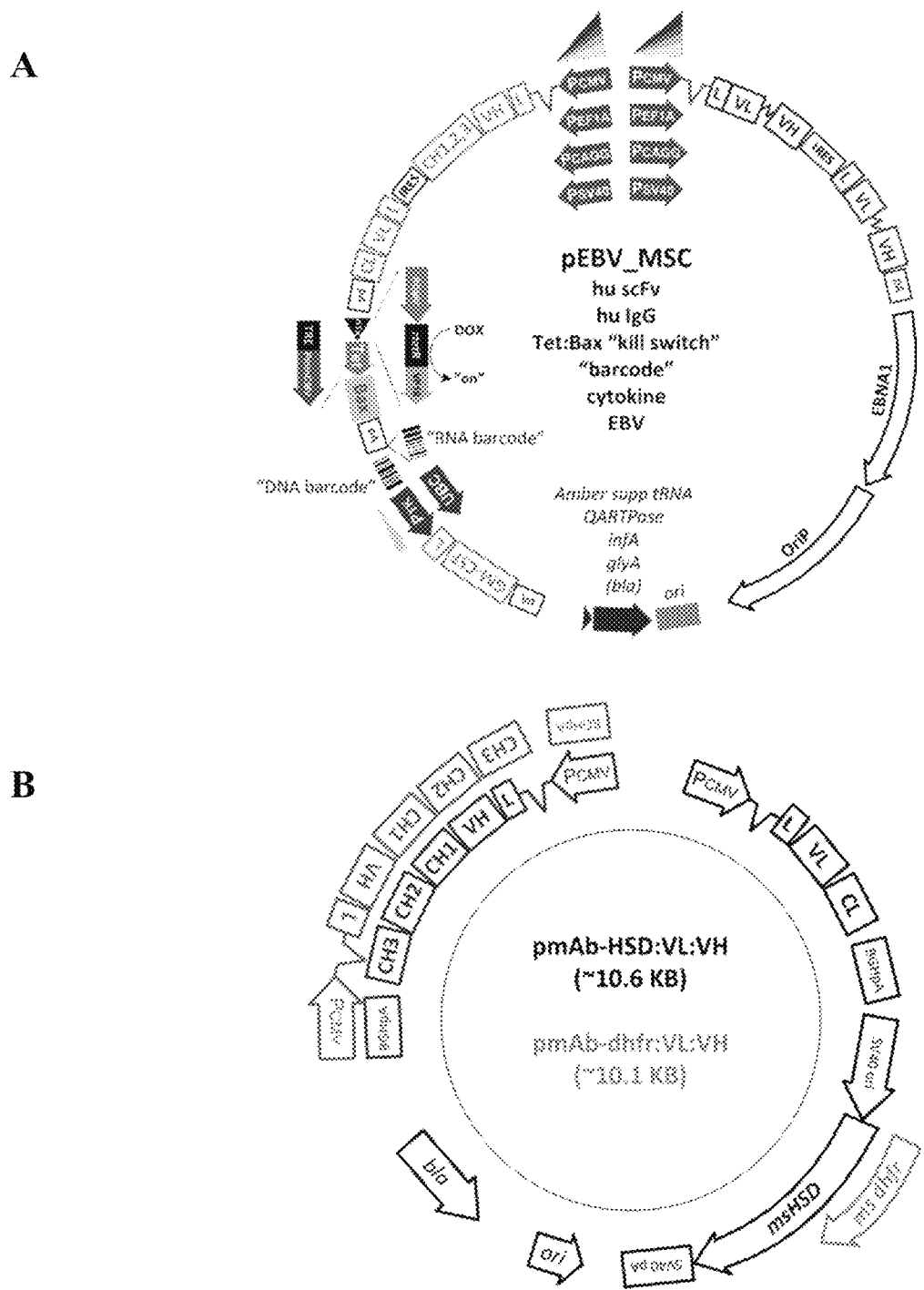
FIG. 2 schematically illustrates an episomal vector for transfecting primary MSC as described herein (Panel A); and a bicistronic vector used to transfect human adipose MSC to express human anti-LASV MAb GP19.7E (Panel B).

Vector design to allow for sufficient levels and duration of expression for protection against challenge. A multicopy, non-infective, non-integrative, circular episome is used to express protective completely human single chain antibody fragments, full length IgGs, or other immunoreactive polypeptides against multiple (potentially hundreds) bacterial, viral, fungal, or parasite proteins or protein toxoids simultaneously (see FIG. 1, which illustrates IgG, ScFV, diabody and tribody-type immunomodulators). In some preferred embodiments, the episome is based on components derived from Epstein-Barr virus (EBV) nuclear antigen 1 expression cassette (EBNA1) and the OriP origin of replication. These preferably are the only components of EBV that are used, so that no viruses are replicated or assembled. This system results in stable extra-chromosomal persistence and long-term ectopic gene expression in mesenchymal stem cells. In the methods described herein, ScFVs or other immunoreactive polypeptides are effectively expressed in and secreted from MSC in protective amounts. A full length LASV neutralizing antibody in hADMSC has been expressed as a proof of concept. The ability of EBV-based episomes to introduce and maintain very large human genomic DNA fragments (>300 kb) in human cells is another significant advantage of the methods described herein. This feature permits cloning of dozens of expression elements in a vector capable of replicating in bacteria, amenable to large scale purification, transfection into hMSC, and replication as an episomal plasmid. Targeted expression levels for the immunoreactive polypeptides (e.g., ScFVs) are about 10 pg/cell/day for each immunoreactive polypeptide, preferably expression levels of 5 pg/cell/day. An infusion with about $1\times10^{11}$ MSC with a productivity rate of 10 pg/cell/day for each immunoreactive polypeptide generates about 1 gram of soluble polypeptide per day, equivalent to a 15 mg/mL level in the circulation of a 75 Kg adult, which is a suitable therapeutic dosage level. Promoters and other regulatory elements are used to drive the expression of each type of immunomodulatory molecule.

Several reports in the literature point to a non-classical pattern of expression from well characterized promoters in MSC. The human cytomegalovirus major immediate early gene promoter (CMV-MIE) is one of the strongest promoters known, and a major element in the generation of multi-gram per liter recombinant protein drug producing stable mammalian cell lines. The CMV-MIE is however, relatively poorly transcribed in MSC. In contrast, EF1A, UBC, and CAGG promoters have demonstrated high levels of expression in MSC without obvious signs or promoter silencing. The episomal vectors utilized in the methods described herein can include any such promoters. FIG. 2, Panel A, provides a schematic illustration of a representative and non-limiting example of a pEBV MSC episomal vector. Expression vectors without antibiotic selection markers also are provided for expansion of plasmids in *E. coli*. The replicative nature of the episomal plasmid precludes its linearization with a restriction endonuclease that disrupts the antibiotic resistance gene's open reading frame. Thus, it is conceivable that genetic rearrangements would result in expression of an antibiotic resistance gene, potentially giving rise to undesirable antibiotic resistance-mediated side effects in humans in selected cases. This scenario can be averted by substituting antibiotic resistance genes with metabolic selectable markers for growth and propagation of plasmids in *E. coli* strains, if needed or desired.

Design of regulatory elements for targeted expression levels of individual therapeutic molecules and shutoff. Regulatory elements in the vector are utilized to accommodate desired secreted levels and serum levels of each immunomodulatory molecule of interest. Expression of full length antibodies, ScFV, or other immunoreactive polypeptides benefit from strong promoters (e.g. CMV, EF1A, CAGG, etc.) to achieve therapeutic serum levels within less than one day after administration of MSCs. Other immunomodulatory molecules, such as cytokines, are often expressed and secreted at low levels, and transiently by MSC. To accommodate required flexibility in disparate levels and timing of expression such genes are driven from low basal promoters (i.e. TK), or through controlled induction from a Tet on/off promoter. The Tet promoter system benefits from the use of innocuous antibiotic analogs such as anhydrotetracycline, which activates the Tet promoter at concentrations 2 logs lower than with tetracycline, does not result in dysregulation of intestinal flora, does not result in resistance to polyketide antibiotics, and does not exhibit antibiotic activity. Anhydrotetracycline is fully soluble in water, and can be administered in drinking rations to potentiate activation of selected genes in transfected MSCs. The potential toxicity of anhydrotetracycline, the first breakdown product of tetracycline in the human body, can be circumvented by administration of other analogs, such doxycycline, an FDA-approved tetracycline analog that also activates the Tet on/off promoter system. This system preferentially is employed in the design of a failsafe "kill switch" by tightly regulating inducible expression of a potent pro-apoptotic gene (e.g. Bax) to initiate targeted apoptosis of transfected MSCs in the event of untoward side effects or when the desired therapeutic endpoint has been achieved. Recent advances in the Tet-on system have resulted in much enhanced repression of promoter leakiness and responsiveness to Dox at concentrations up to 100-fold lower than in the original Tet system (Tet-On Advanced™, Tet-On 3G™). Drug selectable markers are not used to maintain vector stability in transfected MSC: EBV-based vectors, which are known to replicate and be retained in daughter cells at a rate of 90-92% per cell cycle.

Vector safety/immunogenicity studies. Because episomes do not produce replicating viruses, and the cells in which they are expressed do not produce MHC molecules in any significant amounts, episomes do not result in vector-derived immunity that would prevent a subsequent use of the platform in an individual. This can be confirmed by designing a sensitive assay to detect immune responses (antibody ELISA and T-cell based assays) to components derived from Epstein-Barr virus (EBV) nuclear antigen 1 expression cassette, and to the MSC background (HLA typing). Genetic studies are performed to investigate rates of EBV integration into the host cell chromosome (FISH, Southern blot, qPCR), and to measure the transient replicative nature of the vector. It has been reported that EBV vectors retain about 90 to 92% replication per cell cycle in the absence of a selectable marker. A decreasing replication rate contributes to the clearance of the vector from the host system. Compartmentalization of injected MSC is assessed in non-human primates (NHP) by tracking fluorescently labeled cells preloaded with cell membrane permeable dyes (green CMFDA, orange CMTMR) that upon esterification will no longer cross the lipid bilayer and become highly fluorescent. Such measurements are performed on freshly prepared tissue sections (lymph nodes, liver, spleen, muscle, brain, pancreas, kidney, intestine, heart, lung, eye, male and female reproductive tissue) or through whole body scans. Additional tissue sections are processed for isolation of DNA and RNA for analysis of vector sequences and corresponding transcripts. Design of oligos specific for each immunoreactive polypeptide, cytokine, and shutoff transcript permit assessment of individual gene expression in all tissues. Some promoters are more actively transcribed in some tissues than others, requiring assessment of both the preferential localization of MSC to peripheral tissues after injection and MSC residency and the corresponding transcriptional activity of the recombinant genes. To this end, two artificial "barcode" nucleic acids tags can be included, one specific to Tet on/off-driven RNA transcripts, and the other to episomal vector DNA. These tags permit rapid identification of the very unique sequences among the NHP and human genome and transcriptome background (see FIG. 2).

Selection and Design of the Delivery Strategy.

MSC as transient delivery vehicles for therapeutic molecules. MSC are amenable to large scale electroporation, with up to 90% efficiency. MaxCyte, Inc. (Gaithersburg, Md.) markets the "MaxCyte® VLX™ Large Scale Transfection System, a small-footprint, easy to use instrument specifically designed for extremely large volume transient transfection in a sterile, closed transfection environment. Using flow electroporation technology, the MAXCYTE VLX can transfect up to about $2 \times 10^{11}$ cells in less than about 30 minutes with high cell viability and transfection efficiencies in a sterile, closed transfection environment. This cGMP-compliant system is useful for the rapid production of recombinant proteins, from the bench through cGMP pilots and commercial manufacturing". MSC can be grown in chemically defined (CD) media, in large scale cell culture environments. Recent advances in bioprocessing engineering have resulted in rapid development of CD formulations that support large scale expansion of MSC without loss of pluripotent characteristics and retention of genetic stability. Adipose-derived MSC can be readily procured from liposuction procedures, with an average procedure yielding about $1 \times 10^8$ MSC, thus providing sufficient cell numbers for expansion ex vivo prior to banking (approximately 25 doublings, $>3 \times 10^{15}$ cells) with remaining lifespan and number of doublings (approximately 25) sufficient to sustain expression and delivery of therapeutic molecules in vivo for several weeks after infusion. MSC commonly display doubling rates in the 48 to 72 hour range, thus potentially providing in vivo lifespans in the range of 50 to 75 days. The turnover rate of infused MSC can be assessed by measuring circulating levels of transgene products, and by detection of EBV sequences by qPCR in blood, nasal aspirates, and urine, in humans. Essentially complete elimination of MSC after the desired therapeutic timespan can be achieved by inducing self-destruction via controlled inducible expression of pro-apoptotic genes built into the expression vector. Levels of circulating MSC-derived immunoreactive polypeptides or other immunomodulators after injection, and vector induced autoimmunity or GVHD responses in NHP also can be assessed. In humans, additional markers associated with autoimmune or allogeneic immune responses can be measured, such as biomarkers of liver injury (ALT, AST), liver (ALB, BIL, GGT, ALP, etc.) and renal function markers (BUN, CRE, urea, electrolytes, etc.).

Isolation, characterization, and banking MSC for therapeutic use. The lack of expression of lymphohematopoietic lineage antigens distinguishes MSCs from hematopoietic cells, endothelial cells, endothelial progenitors, monocytes, B cells and erythroblasts. Primary MSC are not immortal and thus are subject to the "Hayflick limit" of about 50 divisions for primary cells. Nevertheless, the capacity for expansion is enormous, with one cell capable of producing up to about $10^{15}$ daughter cells. Additionally, MSC have low batch-to-batch variability. Cell bank sizes capable of rapidly protecting millions of at risk individuals can be generated by pooling large numbers of pre-screened donor adipose tissue-derived MSC: 100 donors at $1 \times 10^8$ cells/donor$\times 25$ generations ex vivo=about $3 \times 10^{17}$ cells; at about $1 \times 10^{11}$ cells/infusion=about 3 million doses. Two approaches can be used in the generation of therapeutic MSC banks: (1) isolation, expansion, testing, banking, following by transfection, recovery and administration; and (2) isolation, expansion, testing, transfection, banking to generate ready-to-administer cells upon thawing and short recovery.

For characterization, the master cell bank can be tested for sterility, mycoplasma, in vitro and in vivo adventitious agent testing, retrovirus testing, cell identity, electron microscopy, and a number of specific virus PCR assays (the FDA requires 14 in their 1993 and 1997 guidance documents, and that list has been augmented with several recommended viruses in addition, mainly polyoma viruses). With the potential initial use of serum in primary culture conditions, testing can be performed for the 9CFR panel of bovine viruses. If cells come in contact with porcine products during normal manipulations testing for porcine viruses preferably is performed, as well.

Pharmacokinetics/pharmacodynamics (PK/PD). One of the limitations of using MSC for tissue repair has been the inability of cells to permanently colonize organs after ex vivo expansion and reinjection into the person from which they were derived. MSC circulate for a limited period of time (e.g., several weeks or months), whether injected into MHC matched or unmatched individuals. This particular short-coming in the development of an adult MSC universal gene delivery platform is a benefit in the methods described herein. The pharmacokinetic (PK) profile of each transgene expressed in transfected MSC can be assessed in NHP for each engineered delivery vector platform developed. One single dose PK study desirably is performed in cynomolgus monkeys, with transfected MSC administered IV. In such a study 2 male and 2 female monkeys each are intravenously (i.v.) administered a high dose (about $10^{11}$ cells), intermediate dose (about $10^8$ cells), and a low dose (about $10^5$ cells) of MSC. Endpoints to be evaluated include: cage-side observations, body weight, qualitative food consumption, ophthalmology, electrocardiogram, clinical pathology (e.g., hematology, chemistry, coagulation, urinalysis); immunology (e.g., immunoglobulins and peripheral leukocytes such as B cells, T cells and monocytes); immunogenicity; gross pathology (e.g., necropsy and selected organ weights); histopathology; tissue binding; and pharmacokinetics. Serum concentrations of each recombinant antibody can be monitored over 9 weeks with qualified sandwich type ELISA that utilize antibody-specific capture and detection (HRP-labeled anti-id) reagents on days 1, 3, 6, 12, 24, 36, 48, and 63. PK analyses can be conducted by non-compartmental methods using WINNONLIN software (Pharsight Corp.). Pharmacokinetic parameters for each antibody can be expressed as maximum serum concentration ($C_{max}$), dose normalized serum concentration ($C_{max}/D$), area under the concentration-time curve from time 0 to infinity ($AUC_{0-\infty}$), dose normalized area under the concentration-time curve from time 0 to infinity ($AUC_{0-\infty}/D$), total body clearance (CL), volume of distribution at steady state ($V_{ss}$), apparent volume of distribution during the terminal phase ($V_z$), terminal elimination phase half-life ($t_{1/2,term}$), and mean residence time (MRT). Peripheral circulation and compartmentalization of injected MSC can be assessed in NHP by tracking fluorescently labeled cells preloaded with cell membrane permeable CMFDA or CMTMR dyes, as described above, on freshly prepared tissue sections or through whole body scans. Vector DNA sequences and transcripts can be monitored by qPCR, as outlined above.

Reusability. There is an extensive body of literature outlining the lack of rejection against MSC in vivo. Nonetheless, this phenomenon can be evaluated in NHP with multiple injections of syngeneic MSC modified with homologous and heterologous DNA vectors, followed by immunological profiling of allogeneic responses. For example, one group of NHP can be injected with a bolus of syngeneic MSC transfected with an episomal vector expressing LASV antibodies, and another with a similar vector expressing influenza antibodies. The immune response to the MSC platform and to components of the vector can be assessed weekly over the course of 77 days, during which any immunological response should be detectable. Safety and immunogenicity in NHP following activation of the shutoff mechanism by administration of doxycycline or other tetracycline analogs can be assessed in similar fashion. Following administration of a doxycycline regimen, adverse immunological responses to vector components and the MSC delivery platform can be assessed in a similar fashion, e.g., first semi-daily for the first 2 weeks, then weekly for an additional 77 days. Additional markers of apoptotic cell death can be tracked by established assays, such as increased serum lactic dehydrogenase (LDH) and caspases, and phosphatidyl serine (PS) in circulating MSC. If an immunological response to vector and MSC is not detectable following this 77-day period NHP can be re-injected with homologous MSC, one group with MSC transfected with an homologous vector, whereas the other group will receive a heterologous DNA vector. The homologous and heterologous vectors will have the same background, but with different recombinant antibody repertoires. This approach can demonstrate immunogenicity against the MSC and the expression DNA vector, irrespective of the recombinant antibody repertoire. The 77 day timeline for assessment of immunological reactions against the MSC platform is chosen based on multiple dose toxicokinetic studies with human antibodies in cynomolgus monkeys showing a mean 5000-fold reduction in peak serum levels of recombinant antibody administered at 10 mg/Kg over this time frame. In such studies some NHP may develop anti-human antibody responses around 50 to 60 days following the first administration, while some animals may never develop a detectable humoral response to the heterologous IgG.

Transport of MSC. Desirably, the MSC can be transported in a device that allows for warm chain (37° C.) transport of genetically modified MSC allowing for elimination of cold-chain transport, with increased sample capacity and cell monitoring technologies, such as devices from MicroQ Technologies. These devices maintain precise warm temperatures from about 24 to about 168 hours, thereby allowing sufficient time for deployment of a ready-to-use therapeutic anywhere in the world. Additional capacity for storage and transport of encapsulated cells can be introduced, and capsules capable of supporting gas exchange can be prepared, as needed. The elapsed time from encapsulation to administration will account for metabolic changes in IP-MSC, cell growth rate, changes in viability, and any additional product changes that will impact performance. Demonstration of Transient Protective Immunity.

Challenge studies in macaques infused with MSC expressing protective antibodies. *Cynomolgus macaques* are infused with macaque MSCs expressing anti-LASV GP single chain antibodies, then challenged by IM injection with 1000 plaque forming units (pfu) of LASV virus (Josiah strain), and evaluated as described by Geisbert et al. Animals showing clinical signs consistent with terminal LF are euthanized. Following challenge, bio-samples are processed for measurement of viremia by plaque assay and RT-PCR. Viral RNA is sequenced to identify whether specific mutations in the GPC gene occur upon therapy in NHPs. For any animal that succumbs to challenge, a variety of bio-samples including tissues, blood, and other body fluids are taken for histopathology, immunohistochemistry, virus isolation, and genome detection. Surviving macaques are monitored for humoral responses to viral antigens by conducting a series of Western-blot and ELISA assays to detect evidence of any antibody response to major viral structural proteins (G1, G2, NP, Z). Similar studies with MSC constructs expressing protective antibodies against influenza virus are used for human challenge studies.

The following non-limiting examples are provided to illustrate certain features and aspects of the IP-MSC and methods described herein.

EXAMPLE 1

Lassa Virus (LASV) Neutralizing Antibodies

About thirty milliliters of whole blood were collected from confirmed adult Lassa fever (LF) survivors from Sierra Leone no earlier than 8 weeks following discharge from the hospital, and up to several months of convalescence. Peripheral blood mononuclear cells (PBMC) were isolated from the blood samples by Ficoll gradient centrifugation, cryo-preserved, and transported in dry shippers to the United States. Cultures of the PBMC were plated at low densities in 96-well plates and stimulated with R848 and interleukin-2 (IL-2) for polyclonal activation of B cells. Supernatants from wells showing colony growth after stimulation were screened for human IgG binding to ELISA plates coated with recombinantly-expressed LASV NP, GPC (GP1+GP2), GP1, or Z proteins. Clones with significant reactivity were expanded, cloned, and re-screened. RNA was isolated from B cell clones producing IgG specific to LASV proteins. Human light chain (LC) and heavy chain (HC) genes from the IgG were amplified by RT-PCR, and cloned in linear single chain expression vectors. HEK-293T cells were co-transfected with matched LC and HC constructs to assess expression of individual LASV human monoclonal antibodies (huMAbs) and to purify small quantities of antibody for preliminary in vitro characterization studies.

Frozen PBMCs shipped from Sierra Leone had excellent viability and high frequencies of antibody producing memory B cells. Greater than 75 independent B cell clones to the glycoproteins from different patients were isolated. Binding and specificity profiles of LASV GPC component-specific huMAbs were determined in immunoprecipitation and ELISA assays.

LASV plaque reduction neutralization test (PRNT) assay. Lassa virus (Josiah, GA391, and 803213 strains, for which good guinea pig models exist and are available) may be pre-incubated with various dilutions (e.g., about 10 pM to about 300 nM) of each MAb prior to infection of Vero or Vero E-6 cells. Virus may be removed after infection by washing twice with phosphate-buffered saline (PBS) and cell medium with 0.5% agarose overlay may be added to each culture. Plaques may be counted about 48 hours thereafter following neutral red staining. The level of inhibition is then plotted against concentration and an IC50 (amount of protein required to block 50% entry) can be calculated.

Two identified LASV huMAbs designated as GP10.4B and GP19.7E displayed virus neutralization in vitro in the LASV plaque reduction neutralization test (PRNT) assay. GP19.7E was significantly more potent than 10.4B. The huMAbs GP10.4B and GP19.7E also exhibited significant neutralization potential against live LASV. The heavy chain (HC) and light chain (LC) nucleotide sequences of GP10.4B and GP19.7E are shown in FIG. 3 (HC) and FIG. 4 (LC). The corresponding amino acid sequences are shown in FIG. 5.

EXAMPLE 2

Preparation of Immunoprotective Primary MSC Expressing an Anti-LASV Immunoreactive Polypeptide Adipose tissue-derived MSC were seeded in 6-well plates at a density of about 1 million cells/well in modified Eagle's medium alpha (MEM alpha) medium supplemented with 10% FBS. The following day, cells were transfected with either LIPOFECTAMINE 2000 (Invitrogen) or PEI (Polyplus) and a pCMVintA_17HSD:huMAb 19.7E construct according to manufacturer recommendations: Light and Heavy chain antibody genes from huMAbs GP19.7E was re-engineered with optimal Kozak sequences and deconvolved 5' UTRs, and cloned in a bicistronic mammalian expression vector (FIG. 3, Panel B), in tandem and in opposing orientations. In transiently transfected HEK-293T/17 cells, the opposing orientation gene constructs resulted in higher secreted antibody levels than from tandem counterparts. An NS0 cell line expressing huMAb GP19.7E was generated by transfection with opposing antibody gene constructs. About 48 hours post transfection, supernatants were harvested and serially diluted in 1×PBS/0.1% BSA/0.1% TWEEN-20 for ELISA. Using this method the adipose MSC produced about 60 ng/mL of GP19.7E antibody, versus undetectable signal for an empty vector control.

EXAMPLE 3

Figure 6:
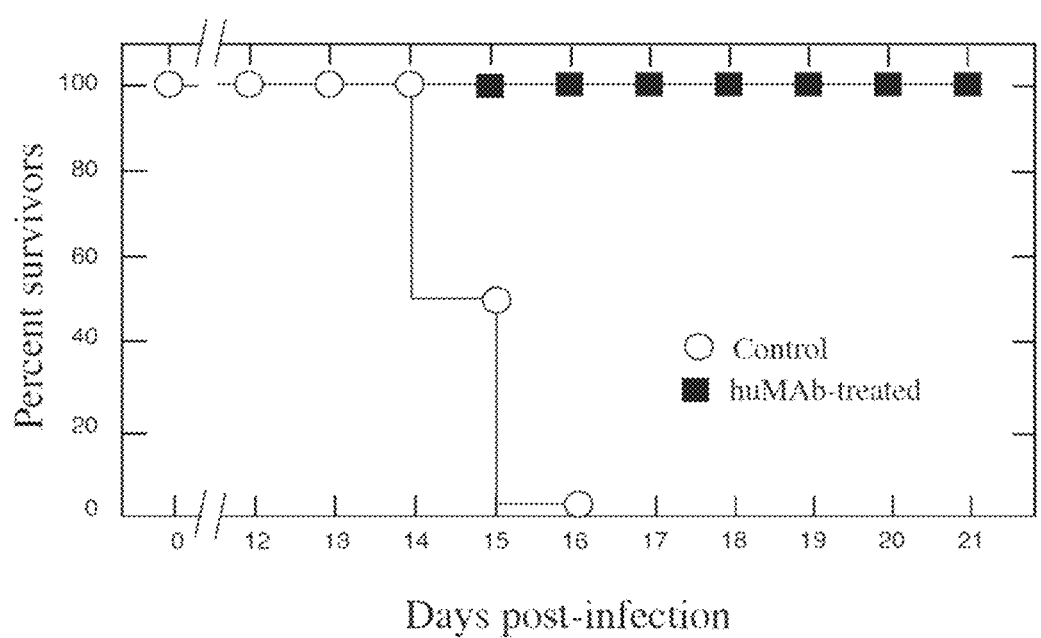
FIG. 6 provides a graph of percentage of survivors versus day post LASV infection for guinea pigs treated with human anti-LASV IgG MAb GP10.4B and human anti-LASV MAb GP19.7E, compared to control guinea pigs treated with antibody-free medium.

LASV Protective Immunity Via Administration of Multiple Neutralizing Anti-LASV Antibodies To demonstrate the immunotherapeutic activity of anti-LASV IgG huMAbs, outbred guinea pigs were injected with a single dose of approximately 30 mg/Kg and 15 mg/Kg of MAb GP19.7E and MAb GP10.4B, respectively, on the same day as LASV challenge. LASV Josiah was adapted to outbred guinea pigs resulting in a uniformly lethal model by the intraperitoneal (i.p.) route. These outbred guinea pigs displayed clinical signs of the disease similar to those observed in the inbred guinea pigs strain 13 and humans. All control guinea pigs injected with antibody-free diluent succumbed with typical signs of Lassa fever by day 16 of the experiment (FIG. 6). The huMAb-treated guinea pigs were followed to 21 days. None of these huMAb-treated animals died or showed any signs of Lassa fever. These results demonstrate that treatment with this combination of Lassa virus glycoprotein specific huMAbs did not merely prolong survival, but provided complete protection from the lethal effects of Lassa virus.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

The following references and any other previously identified references not specifically listed below are incorporated herein by reference in their entirety.

Abraham, E. J., Kodama, S., Lin, J. C., Ubeda, M., Faustman, D. L., and Habener, J. F. (2004). Human pancreatic islet-derived progenitor cell engraftment in immunocompetent mice. *Am J Pathol* 164, 817-830.

Bhargava, A., Mishra, D., Banerjee, S., and Mishra, P. K. (2012). Dendritic cell engineering for tumor immunotherapy: from biology to clinical translation. *Immunotherapy* 4, 703-718.

Cavenaugh, J. S., Awi, D., Mendy, M., Hill, A. V., Whittle, H., and Mcconkey, S. J. (2011). Partially randomized, non-blinded trial of DNA and MVA therapeutic vaccines based on hepatitis B virus surface protein for chronic HBV infection. *PloS one* 6, e14626.

Choi, J. J., Yoo, S. A., Park, S. J., Kang, Y. J., Kim, W. U., Oh, I. H., and Cho, C. S. (2008). Mesenchymal stem cells overexpressing interleukin-10 attenuate collagen-induced arthritis in mice. *Clin Exp Immunol* 153, 269-276.

Gao, J., Dennis, J. E., Muzic, R. F., Lundberg, M., and Caplan, A. I. (2001). The dynamic in vivo distribution of bone marrow-derived mesenchymal stem cells after infusion. *Cells Tissues Organs* 169, 12-20.

Klinge, P. M., Harmening, K., Miller, M. C., Heile, A., Wallrapp, C., Geigle, P., and Brinker, T. (2011). Encapsulated native and glucagon-like peptide-1 transfected human mesenchymal stem cells in a transgenic mouse model of Alzheimer's disease. *Neuroscience letters* 497, 6-10.

Kumar, S., Nagy, T. R., and Ponnazhagan, S. (2010). Therapeutic potential of genetically modified adult stem cells for osteopenia. *Gene therapy* 17, 105-116.

Li, X., Lu, Y., Huang, W., Xu, H., Chen, X., Geng, Q., Fan, H., Tan, Y., Xue, G., and Jiang, X. (2006). In vitro effect of adenovirus-mediated human Gamma Interferon gene transfer into human mesenchymal stem cells for chronic myelogenous leukemia. *Hematological oncology* 24, 151-158.

Loebinger, M. R., and Janes, S. M. (2010). Stem cells as vectors for antitumour therapy. *Thorax* 65, 362-369.

Ohtaki, H., Ylostalo, J. H., Foraker, J. E., Robinson, A. P., Reger, R. L., Shioda, S., and Prockop, D. J. (2008). Stem/progenitor cells from bone marrow decrease neuronal death in global ischemia by modulation of inflammatory/immune responses. *Proc Natl Acad Sci USA* 105, 14638-14643.

Palucka, K., and Banchereau, J. (2012). Cancer immunotherapy via dendritic cells. *Nature reviews. Cancer* 12, 265-277.

Prockop, D. J. (2009). Repair of tissues by adult stem/progenitor cells (MSCs): controversies, myths, and changing paradigms. *Mol Ther* 17, 939-946.

Sasaki, M., Radtke, C., Tan, A. M., Zhao, P., Hamada, H., Houkin, K., Honmou, O., and Kocsis, J. D. (2009). BDNF-hypersecreting human mesenchymal stem cells promote functional recovery, axonal sprouting, and protection of corticospinal neurons after spinal cord injury. *J Neurosci* 29, 14932-14941.

Song, Y. S., Lee, H. J., Doo, S. H., Lee, S. J., Lim, I., Chang, K.-T., and Kim, S. U. (2012). Mesenchymal stem cells over-expressing hepatocyte growth factor (HGF) inhibit collagen deposit and improve bladder function in rat model of bladder outlet obstruction. *Cell Transplantation.*

Wang, Y., Guo, Y., Wang, X., Huang, J., Shang, J., and Sun, S. (2011). Human serum amyloid P functions as a negative regulator of the innate and adaptive immune responses to DNA vaccines. *Journal of immunology* 186, 2860-2870.

Wei, H. J., Wu, A. T. H., Hsu, C. H., Lin, Y. P., Cheng, W. F., Su, C. H., Chiu, W. T., Whang-Peng, J., Douglas, F. L., and Deng, W. P. (2011). The Development of a Novel Cancer Immunotherapeutic Platform Using Tumor-targeting Mesenchymal Stem Cells and a Protein Vaccine. *Molecular Therapy.*

---

We claim:

1. Immunoprotective primary mesenchymal stems cells (IP-MSC) that episomally express immunoreactive polypeptides that specifically target a viral pathogen; the IP-MSC being adipose-derived mesenchymal stem cells transfected with one or more episomal vectors encoding expressible immunoreactive polypeptides that specifically target the pathogen; wherein the immunoreactive polypeptides comprise amino acid sequences from an antigen-binding region of a neutralizing antibody specific for the pathogen; the antigen-binding region amino acid sequences being arranged to specifically bind to and neutralize the pathogen; wherein the viral pathogen is selected from the group consisting of: an adenovirus, a papillomavirus, a hepadnavirus, a parvovirus, a pox virus, Epstein-Barr virus (EBV), cytomegalovirus (CMV), a herpes simplex virus, roseolovirus, varicella zoster virus, a filovirus, a paramyxovirus, an orthomyxovirus, a rhabdovirus, an arenavirus, a coronavirus, a human enterovirus, hepatitis A virus, a human rhinovirus, polio virus, a retrovirus, a rotavirus, a flavivirus, a hepacivirus, and rubella virus; the episomal vector includes an inducible apoptosis gene; the immunoreactive polypeptides comprise the complementarity determining regions of the antibody; and the one or more episomal vectors are non-infective, non-integrative, circular episomal vectors.

2. The IP-MSC of claim 1, wherein the IP-MSC also express one or more other immunomodulating agents.

3. The IP-MSC of claim 2, wherein the one or more immunomodulating agents are selected from interleukins and interferons.

4. The IP-MSC of claim 3, wherein the one or more immunomodulating agents are selected from IL-2, IL-4, IL-6, IL-7, IL-9, IL-12, IFN$\alpha$, IFN$\beta$, and IFN$\omega$.

5. The IP-MSC of claim 1, wherein the immunoreactive polypeptides are selected from a full-length antibody, an antibody single-chain variable antibody fragment (ScFV), a monovalent antibody antigen-binding fragment (Fab), a divalent antibody antigen-binding fragment (F(ab')$_2$), a diabody, and a tribody.

6. The IPMSC of claim 1, wherein the one or more episomal vectors also encode a tetracycline-controlled transcriptional activation system for activating the inducible apoptosis gene.

7. A pharmaceutical composition for treating or preventing an infection caused by the pathogen, the composition comprising the IP-MSC of claim 1 in a pharmaceutically acceptable carrier.

8. The composition of claim 7, wherein the immunoreactive polypeptides are selected from a full-length antibody, an antibody single-chain variable antibody fragment (ScFV), a monovalent antibody antigen-binding fragment (Fab), a divalent antibody antigen-binding fragment (F(ab')$_2$), a diabody, and a tribody.

9. A method for treating or preventing an infection caused by the pathogen, the method comprising administering to a subject an effective dosage of the IP-MSC of claim 1.

10. The method of claim 9, wherein the immunoreactive polypeptides are selected from a full-length antibody, an antibody single-chain variable antibody fragment (ScFV), a monovalent antibody antigen-binding fragment (Fab), a divalent antibody antigen-binding fragment (F(ab')$_2$), a diabody, and a tribody.

11. Immunoprotective primary mesenchymal stems cells (IP-MSC) that episomally express immunoreactive polypeptides that specifically target cytomegalovirus (CMV); the IP-MSC being adipose-derived mesenchymal stem cells transfected with one or more episomal vectors encoding expressible immunoreactive polypeptides that specifically target CMV; wherein the immunoreactive polypeptides comprise amino acid sequences from an antigen-binding region of a neutralizing antibody specific for CMV; the antigen-binding region amino acid sequences being arranged to specifically bind to and neutralize CMV; wherein the episomal vector includes an inducible apoptosis gene; the immunoreactive polypeptides comprise the complementarity determining regions of the antibody; and the one or more episomal vectors are non-infective, non-integrative, circular episomal vectors.

12. The IP-MSC of claim 11, wherein the IP-MSC also express one or more other immunomodulating agents.

13. The IP-MSC of claim 12, wherein the one or more immunomodulating agents are selected from interleukins and interferons.

14. The IP-MSC of claim 13, wherein the one or more immunomodulating agents are selected from IL-2, IL-4, IL-6, IL-7, IL-9, IL-12, IFN$\alpha$, IFN$\beta$, and IFN$\omega$.

15. The IP-MSC of claim 11, wherein the immunoreactive polypeptides are selected from a full-length antibody, an antibody single-chain variable antibody fragment (ScFV), a monovalent antibody antigen-binding fragment (Fab), a divalent antibody antigen-binding fragment (F(ab')$_2$), a diabody, and a tribody.

16. The IPMSC of claim 11, wherein the one or more episomal vectors also encode a tetracycline-controlled transcriptional activation system for activating the inducible apoptosis gene.

17. A pharmaceutical composition for treating or preventing a CMV infection, the composition comprising the IP-MSC of claim 11 in a pharmaceutically acceptable carrier.

18. The composition of claim 17, wherein the immunoreactive polypeptides are selected from a full-length antibody, an antibody single-chain variable antibody fragment (ScFV), a monovalent antibody antigen-binding fragment (Fab), a divalent antibody antigen-binding fragment (F(ab')$_2$), a diabody, and a tribody.

19. A method for treating or preventing a CMV infection, the method comprising administering to a subject an effective dosage of the IP-MSC of claim 11.

20. The method of claim 19, wherein the immunoreactive polypeptides are selected from a full-length antibody, an antibody single-chain variable antibody fragment (ScFV), a monovalent antibody antigen-binding fragment (Fab), a divalent antibody antigen-binding fragment (F(ab')$_2$), a diabody, and a tribody.

* * * * *

UNITED STATES PATENT AND TRADEMARK OFFICE
CERTIFICATE OF CORRECTION

PATENT NO. : 11,123,427 B2
APPLICATION NO. : 16/426911
DATED : September 21, 2021
INVENTOR(S) : Robert F. Garry et al.

Page 1 of 1

It is certified that error appears in the above-identified patent and that said Letters Patent is hereby corrected as shown below:

In the Specification

IN THE CROSS-REFERENCE TO RELATED APPLICATIONS
Column 1, Line 11, delete "9,101,587" and insert --9,101,597--.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 8

<210> SEQ ID NO 1
<211> LENGTH: 671
<212> TYPE: DNA
<213> ORGANISM: Artificial Sequence
<220> FEATURE:
<223> OTHER INFORMATION: huMAb GP10.4B monoclonal antibody heavy chain
<221> NAME/KEY: misc_feature
<222> LOCATION: 1, 12
<223> OTHER INFORMATION: n = A,T,C or G

<400> SEQUENCE: 1
ntgcgcgtta cngatccaag ctgtgaccgg cgcctacctg agatcaccgg tgctagcacc       60
atggagacag acacactcct gctatgggta ctgctgctct gggttccagg ttccactggt      120
gaccaggtgc agctggtaca gtctggggga ggcgtggtcc agcctgggag gtccctgaga      180
gtctcctgtg ttacgtctgg attcaatttc agagcctacg gcatgcactg ggtccgccag      240
attccaggca agggactgga gtgggtggca gatatttggt ctgccgagac taatagacac      300
tatgcagatt ccgtgaaggg ccgattcacc atctccagag acaactccaa gagcacactg      360
tatctgcaaa tgaacagcct gagagccgag gacacgggcg tatatttctg tgccaaagcg      420
cgaccaggct atgattatgt cgttgactta tggggccagg gaacgctggt catcgtctcc      480
tcagcttcca ccaagggccc atcggtcttc cccctggcgc cctgctccag gagcacctct      540
gggggcacag cggccctggg ctgcctggtc aaggactact ccccgaacc ggtgacggtg       600 tcgtggaact caggcgccct gaccagcggc gtgcacacct tcccggctgt cctacagtcc      660
tcaggactct a                                                           671

<210> SEQ ID NO 2
<211> LENGTH: 819
<212> TYPE: DNA
<213> ORGANISM: Artificial Sequence
<220> FEATURE:
<223> OTHER INFORMATION: huMAb GP 19.7E monoclonal antibody heavy chain

<400> SEQUENCE: 2
atccagctgt gaccggcgcc tacctgagat caccggtgct agcaccatgg agacagacac       60
actcctgcta tgggtactgc tgctctgggt tccaggttcc actggtgacg aggtgcagct      120
ggtggagtct gggggaggct tagttcggcc tgggggggtcc ctgagactct cctgtgcagc    180
ctctggattc tccttcagta gctactcgat gcactgggtc cgccatgttc ctgggaaggg      240
gctggtgtgg gtctcatata ttaatagtga tgggagtact aaaatctacg cggactccgt      300
gaagggccga ttctccatct ccagagacaa tgccaagaac aagctctatc tgcaaatgga      360
cagtttgaga gtcgaggaca cggctgtata ttcgtgtgta aggcttgtac attacgactg      420
```

```
gtccccattc gtgtggggcc agggaaccct ggtcaccgtc tcctcagcct ccaccaaggg    480
cccatcggtc ttccccctgg caccctcctc caagagcacc tctgggggca gcggcccct    540 gggctgcctg gtcaaggact acttccccga accggtgacg gtgtcgtgga actcaggcgc    600
cctgaccagc ggcgtgcaca ccttcccggc tgtcctacag tcctcaggac tctactccct    660
cagcagcgtg gtgaccgtgc cctccagcag cttgggcacc cagacctaca tctgcaacgt    720
gaatcacaag cccagcaaca ccaaggtgga caagaaagtt gagccccaat cttgtgacaa    780
aactcacaca tgcccaccgt gcccagcacc tgaactcct                          819
```

```
<210> SEQ ID NO 3
<211> LENGTH: 732
<212> TYPE: DNA
<213> ORGANISM: Artificial Sequence
<220> FEATURE:
<223> OTHER INFORMATION: huMAb GP10.4B monoclonal antibody light chain
<221> NAME/KEY: misc_feature
<222> LOCATION: 7, 9, 10, 11, 16
<223> OTHER INFORMATION: n = A,T,C or G

<400> SEQUENCE: 3
gcgccgntnn natccnagct gtgaccggcg cctacctgag atcaccggtg ctagcaccat    60
ggagacagac acactcctgc tatgggtact gctgctctgg gttccaggtt ccactggtga    120
cgaaattgtg ttgacacagt ctccatcctc actgtctgcg tctgtaggag acagagtcac    180
catcacttgt cgggcgagtc gggacatcaa tacttattta ggttggtttc agcagagacc    240
agggaaagcc cctaagtccc tgatctatgg tgcatctaat ttgcaaaatg ggtcccatc    300 aaggttcagc ggcagtggat ctgggacgta ttttactctc accatcaacg gcctgcagac    360
tgaagacttt gcgacttatt attgccaaca atatagcatc tacccgctca gtctcggcgg    420
agggaccaag gcggacatga agcgaactgt ggctgcacca tctgtcttca tcttcccgcc    480
atctgatgag cagttgaaat ctggaactgc ctctgttgtg tgcctgctga ataacttcta    540
tcccagagag gccaaagtac agtggaaggt ggataacgcc ctccaatcgg gtaactccca    600
ggagagtgtc acagagcagg acagcaagga cagcacctac agcctcagca gcaccctgac    660
gctgagcaaa gcagactacg agaaacacaa agtctacgcc tgcgaagtca cccatcaggg    720
cctgagctcg cc                                                       732
```

```
<210> SEQ ID NO 4
<211> LENGTH: 891
<212> TYPE: DNA
<213> ORGANISM: Artificial Sequence
<220> FEATURE:
<223> OTHER INFORMATION: huMAb GP19.7E monoclonal antibody light chain

<400> SEQUENCE: 4
cgttcgatcc agctgtgacc ggcgcctacc tgagatcacc ggtgctagca ccatggagac    60
agacacactc ctgctatggg tactgctgct ctgggttcca ggttccactg gtgacgatat    120
tgtgatgacc cagtctccct tccaccctgtc tgcatctgta ggagacagag tcaccatcac    180
ttgccgggcc agtcagagta ttaataattg gttggcctgg tatcaggaga accagggaa    240 agcccctaag ctcctgataa ataaggcgtc tagtttagaa agtggggtcc catcaaggtt    300
cagcggcagt ggatctggga cagaattcac tctcaccatc accagcctgc agcctgatga    360
ttttgcaact tattactgcc aacaatataa tagtaattcg tggacgttcg gccaagggac    420
caaggtggac atgaaacgaa ctgtggctgc accatctgtc ttcatcttcc cgccatctga    480
```

```
tgagcagttg aaatctggaa ctgcctctgt tgtgtgcctg ctgaataact tctatcccag    540
agaggccaaa gtacagtgga aggtggataa cgccctccaa tcgggtaact cccaggagag    600
tgtcacagag caggacagca aggacagcac ctacagcctc agcagcaccc tgacgctgag    660
caaagcagac tacgagaaac acaaagtcta cgcctgcgaa gtcacccatc agggcctgag    720
ctcgcccgtc acaaagagct tcaacagggg agagtgttag agggagctag ctcgacatga    780
taagatacat tgatgagttt ggacaaacca caactagaat gcagtgaaaa aaatgctttt    840
tttgtgaaat ttgtgatgct attgctttat ttgtgaaatt tgtgatgcta t             891
```

<210> SEQ ID NO 5
<211> LENGTH: 204
<212> TYPE: PRT
<213> ORGANISM: Artificial Sequence
<220> FEATURE:
<223> OTHER INFORMATION: huMAb GP10.4B monoclonal antibody heavy chain
<221> NAME/KEY: VARIANT
<222> LOCATION: 204
<223> OTHER INFORMATION: Xaa = Unknown

<400> SEQUENCE: 5

Met Glu Thr Asp Thr Leu Leu Leu Trp Val Leu Leu Trp Val Pro
1               5                   10                  15

Gly Ser Thr Gly Asp Gln Val Gln Leu Val Gln Ser Gly Gly Val
            20                  25                  30

Val Gln Pro Gly Arg Ser Leu Arg Val Ser Cys Val Thr Ser Gly Phe
        35                  40                  45

Asn Phe Arg Ala Tyr Gly Met His Trp Val Arg Gln Ile Pro Gly Lys
    50                  55                  60

Gly Leu Glu Trp Val Ala Asp Ile Trp Ser Ala Glu Thr Asn Arg His
65                  70                  75                  80

Tyr Ala Asp Ser Val Lys Gly Arg Phe Thr Ile Ser Arg Asp Asn Ser
                85                  90                  95

Lys Ser Thr Leu Tyr Leu Gln Met Asn Ser Leu Arg Ala Glu Asp Thr
            100                 105                 110

Gly Val Tyr Phe Cys Ala Lys Ala Arg Pro Gly Tyr Asp Tyr Val Val
        115                 120                 125

Asp Leu Trp Gly Gln Gly Thr Leu Val Ile Val Ser Ser Ala Ser Thr
    130                 135                 140

Lys Gly Pro Ser Val Phe Pro Leu Ala Pro Cys Ser Arg Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Xaa
        195                 200

<210> SEQ ID NO 6
<211> LENGTH: 257
<212> TYPE: PRT
<213> ORGANISM: Artificial Sequence
<220> FEATURE:
<223> OTHER INFORMATION: huMAb GP19.7E monoclonal antibody heavy chain

<400> SEQUENCE: 6

Met Glu Thr Asp Thr Leu Leu Leu Trp Val Leu Leu Trp Val Pro
1               5                   10                  15

```
Gly Ser Thr Gly Asp Glu Val Gln Leu Val Glu Ser Gly Gly Gly Leu
            20                  25                  30

Val Arg Pro Gly Gly Ser Leu Arg Leu Ser Cys Ala Ala Ser Gly Phe
            35                  40                  45

Ser Phe Ser Ser Tyr Ser Met His Trp Val Arg His Val Pro Gly Lys
50                  55                  60

Gly Leu Val Trp Val Ser Tyr Ile Asn Ser Asp Gly Ser Thr Lys Ile
65                  70                  75                  80

Tyr Ala Asp Ser Val Lys Gly Arg Phe Ser Ile Ser Arg Asp Asn Ala
                85                  90                  95

Lys Asn Lys Leu Tyr Leu Gln Met Asp Ser Leu Arg Val Glu Asp Thr
            100                 105                 110

Ala Val Tyr Ser Cys Val Arg Leu Val His Tyr Asp Trp Ser Pro Phe
            115                 120                 125

Val Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
            210                 215                 220

Val Asn His Lys Pro Ser Asn Thr Lys Val Asp Lys Lys Val Glu Pro
225                 230                 235                 240

Gln Ser Cys Asp Lys Thr His Thr Cys Pro Pro Cys Pro Ala Pro Glu
                245                 250                 255

Leu

<210> SEQ ID NO 7
<211> LENGTH: 224
<212> TYPE: PRT
<213> ORGANISM: Artificial Sequence
<220> FEATURE:
<223> OTHER INFORMATION: huMAb GP10.4B monoclonal antibody light chain

<400> SEQUENCE: 7

Met Glu Thr Asp Thr Leu Leu Leu Trp Val Leu Leu Leu Trp Val Pro
1               5                   10                  15

Gly Ser Thr Gly Asp Glu Ile Val Leu Thr Gln Ser Pro Ser Ser Leu
            20                  25                  30

Ser Ala Ser Val Gly Asp Arg Val Thr Ile Thr Cys Arg Ala Ser Arg
            35                  40                  45

Asp Ile Asn Thr Tyr Leu Gly Trp Phe Gln Gln Arg Pro Gly Lys Ala
        50                  55                  60

Pro Lys Ser Leu Ile Tyr Gly Ala Ser Asn Leu Gln Asn Gly Val Pro
65                  70                  75                  80

Ser Arg Phe Ser Gly Ser Gly Ser Gly Thr Tyr Phe Thr Leu Thr Ile
                85                  90                  95

Asn Gly Leu Gln Thr Glu Asp Phe Ala Thr Tyr Tyr Cys Gln Gln Tyr
            100                 105                 110
```

```
Ser Ile Tyr Pro Leu Ser Leu Gly Gly Thr Lys Ala Asp Met Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220
```

<210> SEQ ID NO 8
<211> LENGTH: 235
<212> TYPE: PRT
<213> ORGANISM: Artificial Sequence
<220> FEATURE:
<223> OTHER INFORMATION: huMAb GP19.7E monoclonal antibody light chain

<400> SEQUENCE: 8

```
Met Glu Thr Asp Thr Leu Leu Leu Trp Val Leu Leu Leu Trp Val Pro
1               5                   10                  15

Gly Ser Thr Gly Asp Asp Ile Val Met Thr Gln Ser Pro Ser Thr Leu
            20                  25                  30

Ser Ala Ser Val Gly Asp Arg Val Thr Ile Thr Cys Arg Ala Ser Gln
        35                  40                  45

Ser Ile Asn Asn Trp Leu Ala Trp Tyr Gln Glu Lys Pro Gly Lys Ala
    50                  55                  60

Pro Lys Leu Leu Ile Asn Lys Ala Ser Ser Leu Glu Ser Gly Val Pro
65                  70                  75                  80

Ser Arg Phe Ser Gly Ser Gly Ser Gly Thr Glu Phe Thr Leu Thr Ile
                85                  90                  95

Thr Ser Leu Gln Pro Asp Asp Phe Ala Thr Tyr Tyr Cys Gln Gln Tyr
            100                 105                 110

Asn Ser Asn Ser Trp Thr Phe Gly Gln Gly Thr Lys Val Asp Met Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```